United States Patent
Schoenleber et al.

(10) Patent No.: US 11,186,608 B2
(45) Date of Patent: Nov. 30, 2021

(54) SOLID PHASE SYNTHESIS OF ACYLATED PEPTIDES

(71) Applicant: BACHEM HOLDING AG, Bubendorf (CH)

(72) Inventors: Ralph O. Schoenleber, Lupsingen (CH); Guenther Loidl, Rheinfelden (DE)

(73) Assignee: Bachem Holding AG, Bubendorf (CH)

( * ) Notice: Subject to any disclaimer, the term of this patent is extended or adjusted under 35 U.S.C. 154(b) by 0 days.

(21) Appl. No.: 16/955,532

(22) PCT Filed: Jul. 10, 2018

(86) PCT No.: PCT/EP2018/068696
§ 371 (c)(1),
(2) Date: Jun. 18, 2020

(87) PCT Pub. No.: WO2019/120639
PCT Pub. Date: Jun. 27, 2019

(65) Prior Publication Data
US 2021/0009631 A1    Jan. 14, 2021

(30) Foreign Application Priority Data
Dec. 21, 2017   (EP) .................................... 17209828

(51) Int. Cl.
    *C07K 1/00*    (2006.01)
    *C07K 1/06*    (2006.01)
    *C07K 14/605*    (2006.01)
    *A61K 38/00*    (2006.01)

(52) U.S. Cl.
CPC .............. *C07K 1/063* (2013.01); *C07K 1/006* (2013.01); *C07K 14/605* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,753,206 A | 5/1998 | McBride et al. | |
| 2019/0010204 A1 | 1/2019 | Chen et al. | |

FOREIGN PATENT DOCUMENTS

| | | |
|---|---|---|
| CN | 103848910 A | 6/2014 |
| CN | 104356224 A | 2/2015 |
| CN | 105753964 A | 7/2016 |
| CN | 106478806 A | 3/2017 |
| WO | 2006/097537 A2 | 9/2006 |
| WO | 2010/029159 A1 | 3/2010 |
| WO | 2013/128003 A1 | 9/2013 |
| WO | 2016/005960 A1 | 1/2016 |
| WO | 2016/046753 A1 | 3/2016 |
| WO | 2017/114191 A1 | 7/2017 |

OTHER PUBLICATIONS

Guryanov Ivan et al.: "Innovative chemical synthesis and conformational hint on the lipopeptide liraglutide", Journal of peptide Science, vol. 22, No. 7, Jul. 1, 2016, pp. 471-479.
Cóngora-Benitez et al., Chem. Comm., 2012, 48:2313-2315.
Thieriet et al., Terahedron Letters, 1997, 38:7275-7278.
Isidro-Llobet et al., Chemical Reviews, 2009, 109:2455-2504.
International Preliminary Report on Patentability in International Application No. PCT/EP2018/068696, dated Jul. 2, 2020.

*Primary Examiner* — Jeanette M Lieb
(74) *Attorney, Agent, or Firm* — J.A. Lindeman & Co. PLLC

(57) ABSTRACT

The present invention relates to methods and compounds for the solid phase synthesis of peptides carrying a substituent at an amino group of an amino acid side chain.

17 Claims, No Drawings
Specification includes a Sequence Listing.

```
                    SEQUENCE LISTING

<160> NUMBER OF SEQ ID NOS: 2

<210> SEQ ID NO 1
<211> LENGTH: 31
<212> TYPE: PRT
<213> ORGANISM: Artificial Sequence
<220> FEATURE:
<223> OTHER INFORMATION: semaglutide, glucagon-like peptide 1 (GLP1)
      analogue
<220> FEATURE:
<221> NAME/KEY: X
<222> LOCATION: (2)..(2)
<223> OTHER INFORMATION: 2-aminoisobutyric acid (Aib)

<400> SEQUENCE: 1

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

SOLID PHASE SYNTHESIS OF ACYLATED PEPTIDES

The present invention relates to the field of peptide synthesis at an industrial or laboratory scale. Improved methods for peptide modification (e.g. acylation) are disclosed. The present invention is directed to methods of effectively synthesizing peptides having complex substituents at an amino group of an amino acid side chain. Preferred embodiments relate to the synthesis of peptides, where the amino group of an amino acid side chain is acylated.

Modifications of side-chain amino groups and in particular the acylation of side-chain amino groups are found in naturally occurring as well as in man-made peptides. They may modify a peptide's properties, e.g. its stability against enzymatic degradation and circulation lifetime in the bloodstream. Therefore, methods for the efficient synthesis of acylated peptides are of great interest, e.g. for the manufacture of therapeutic peptides.

In other preferred embodiments, the present invention refers to the complete solid phase synthesis of semaglutide. Semaglutide belongs to the group of glucagon-like peptides. It is an analog of human glucagon-like peptide 1 GLP1(7-37), where alanine in position 2 (8) has been exchanged against alpha-Amino-isobutyric acid (Aib), and lysine in position 28 (34) has been exchanged against arginine. Further, the lysine in position 20 (26) is acylated by a complex side chain.

The primary amino acid of semaglutide, a glucagon-like peptide 1 (GLP1) analogue, is given in one letter code below.

(SEQ ID NO: 1)
H(Aib)EGTFTSDVSSYLEGQAAKEFIAWLVRGRG

This sequence is derived from the glucagon-like peptide 1 (GLP1) wild type peptide:

(SEQ ID NO: 2)
HAEGTFTSDVSSYLEGQAAKEFIAWLVKGRG

Chemical peptide synthesis in general is well-known in the art and usually proceeds from the peptide's C-terminus to the N-terminus (cf., brochure "Solid Phase Peptide Synthesis Bachem—Pioneering Partner for Peptides", published by Global Marketing, Bachem group, June 2014). During synthesis, formation of the peptide bond between the alpha amino group of the first amino acid and the alpha carboxyl group of a second amino acid should be favored over unintended side reactions. This is commonly achieved by the use of "permanent" and "temporary" protecting groups. The former are used to block reactive amino acid side chains and the C-terminal carboxyl group of the growing peptide chain and are only removed at the end of the entire synthesis. The latter are used to block the alpha amino group of the second amino acid during the coupling step, thereby avoiding, e.g., peptide bond formation between multiple copies of the second amino acid. Two standard approaches to chemical peptide synthesis can be distinguished, namely Liquid Phase Peptide Synthesis (LPPS) and Solid Phase Peptide Synthesis (SPPS). In addition to LPPS and SPPS, hybrid approaches can be utilized, where fragments are first synthesized by one of the above techniques and then joined together using the other approach. This strategy is typically employed for large peptides with challenging sequences.

LPPS, also referred to as Solution Peptide Synthesis, takes place in a homogenous reaction medium. Successive couplings yield the desired peptide. Virtually no standard protocol exists and careful planning is required to select from a variety of possible protecting group combinations, coupling methods, and solvents. LPPS usually involves the isolation, characterization, and—where desired—purification of intermediates after each coupling. Longer peptides are commonly synthesized by convergent approaches, where several fragments are assembled in parallel and finally combined to yield the end product.

In SPPS, a peptide anchored by its C-terminus to an insoluble polymer resin is assembled by the successive addition of the protected amino acids constituting its sequence.

Successive cycles of amino acid addition are carried out, each consisting of: a) cleavage of the Na-protecting group from the resin-bound peptide, b) washing steps, c) coupling of a protected amino acid, and d) washing steps. Because the growing chain is bound to the insoluble support, the excess of reagents and soluble by-products can be removed by simple filtration. Washing steps with appropriate solvents ensure the complete removal of cleavage agents after the deprotection step a) as well as the elimination of excesses of reagents and soluble by-products resulting from the coupling step c). At the end of the synthesis, the peptide is cleaved from the resin and protecting groups are removed (cf., brochure "Solid Phase Peptide Synthesis Bachem—Pioneering Partner for Peptides", published by Global Marketing, Bachem group, June 2014).

The so-called Fmoc SPPS relies on the use of 9-fluorenylmethyloxycarbonyl (Fmoc) as the temporary amino protecting group and is the most popular form of SPPS. Contrary to LPPS, peptide purification can only be performed at the end of the synthesis, after cleavage from the resin. This is often disadvantageous in particular for the synthesis of large peptides, where various, resin-bound side products can accumulate and render the purification of the final product very challenging. When developing an SPPS process for industrial manufacture, it is therefore imperative to optimize the purity of the raw peptide product.

The synthesis of Semaglutide is described by documents WO 2006/097537, CN-A 104356224, CN-A 106478806, WO 2017/114191, CN-A 105753964, CN-A 103848910 and WO 2016/046753. Fully SPPS based approaches, recombinant approaches with subsequent introduction of the substituent at Lys 20 (26), and hybrid approaches have been proposed.

It is however desirable to provide improved methods for the large scale preparation of acylated peptides in general and of semaglutide in particular. The synthesis of semaglutide is challenging for several reasons: First, like most glucagon-like peptides, semaglutide tends to aggregate. Second, the introduction of the substituent may result in unwanted side reactions, notably in racemization of the N-terminal His moiety. Third, the introduction of Aib by Fmoc-SPPS tends impair peptide yield and purity.

The present application addresses these problems and provides a method for synthesizing peptides having complex substituents at an amino group of an amino acid side in general. In particular, a method for the complete synthesis of semaglutide by SPPS with good yield and purity is disclosed.

In general terms, the present invention comprises a method for the full chemical synthesis of a peptide P, which carries a substituent S at an amino group of an amino acid side chain, the method involving:

a) Providing a compound of the Formula (vii) below:

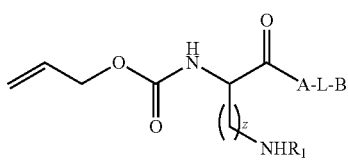

Formula (vii)

wherein:
R₁ is an amino protecting group;
z is an integer from 0 to 10;
B is a solid phase functionalized with any suitable linker structure L; and
A is any peptide sequence of 1 to 100 amino acids, which optionally carry side chain protecting groups, b) Removing the amino protecting group R₁ from the compound of formula (vii);
c) Binding the desired substituent S to the free amino group obtained in step b), wherein the desired substituent S is bound either in one single reaction or in a stepwise fashion to the solid-phase bound peptide, optionally wherein the substituent S carries protective groups;
d) Removing the Alloc protecting group from the solid-phase bound compound obtained in step c);
e) Adding any N-terminal amino acid sequence of 1 to 100 amino acids, which optionally carry side chain protecting groups, to the free alpha amino group obtained in step d) so as to obtain the complete amino acid sequence of peptide P; and
f) Cleaving the peptide P from the solid phase.

The substituent S may in principle be bound by any covalent bound to the free amino group obtained in step b). Most commonly, the binding of the substituent S will represent an acylation, i.e. it will result in the formation of an amide of a carboxylic acid. Inter alia, the methods of the present invention therefore allow the synthesis of branched peptides, PEGylated peptides, and of peptides carrying any type of simple or complex substituent at the side chain amino group obtained in step b). The substituent S may be of any chemical structure, and may inter alia include or consist of mono- or polysaccharides, fatty acid moieties such as palmitoyl moieties or myristoyl moieties, dicarboxylic acid moieties, prenyl moieties, polyethylene glycol (PEG) moieties, amino acid moieties such as glutamyl moieties (e.g. gamma-glutamyl moieties), Poly(styrene-co-maleic acid anhydride) moieties, polysialic acid moieties, hydroxyethyl starch moieties. In a preferred embodiment, the substituent S is an AEEAc-AEEAc-γ-Glu-17-carboxy-heptadecanoyl moiety.

In particular, the present invention comprises a method for the full chemical synthesis of a peptide P, which carries a substituent S at an amino group of an amino acid side chain, the method involving:

a) Providing a compound of the Formula (vii) below:

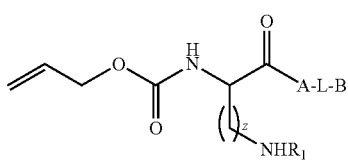

Formula (vii)

wherein:
R₁ is an amino protecting group;
z is an integer from 0 to 10;
B is a solid phase functionalized with any suitable linker structure L; and
A is any peptide sequence of 0 to 100 amino acids, which optionally carry side chain protecting groups, b) Removing the amino protecting group R₁ from the compound of formula (vii);
c) Acylating the free amino group obtained in step b) so as to conjugating the desired substituent S in one single reaction or in a stepwise fashion to the solid-phase bound peptide (i.e., introducing the substituent S into the compound of formula (vii)), optionally wherein the substituent S carries protective groups;
d) Removing the allyloxycarbonyl (Alloc) protecting group from the solid-phase bound peptide obtained in step c);
e) Adding any N-terminal amino acid sequence of 0 to 100 amino acids, which optionally carry side chain protecting groups, to the free alpha amino group obtained in step d) so as to obtain the complete amino acid sequence of peptide P; and
f) Cleaving the peptide P from the solid phase (typically, cleaving the semaglutide peptide from the solid phase and (concomitantly) cleaving the protecting groups from the semaglutide peptide (deprotection)).

In a particularly preferred embodiment, at each occurrence as used herein, a step of cleaving a peptide from the solid support as used in the methods of the present invention also includes the step of cleaving the protecting groups from the semaglutide peptide (deprotection).

In particular, the present invention relates to a method for the full chemical synthesis of a semaglutide peptide, the method involving:

a) Synthesizing a first solid-phase bound peptide sequence of the formula (i) Formula (i):

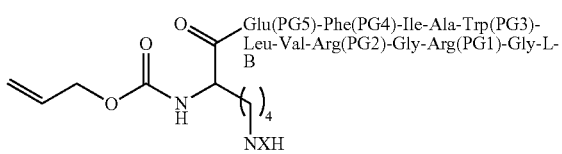

wherein:
X is an amino protecting group R₁ or is an amide bonded 8-amino-3,6-dioxa-octanoic acid moiety having an R₁ protected amino group (AEEAc-R₁) B is a solid phase functionalized with any suitable linker structure L; and PG1 through PG5 independently are the same as or different from any of each other and are H or side-chain protecting groups;

b) Removing the protecting group R₁ so as to expose a free amino group;

c) Acylating said free amino group so as to obtain a second solid-phase bound peptide sequence of the formula (ii), wherein R5 and R6 are the same or different and are H or a carboxyl protecting group; and PG1-5, L and B are as defined above Formula (ii):

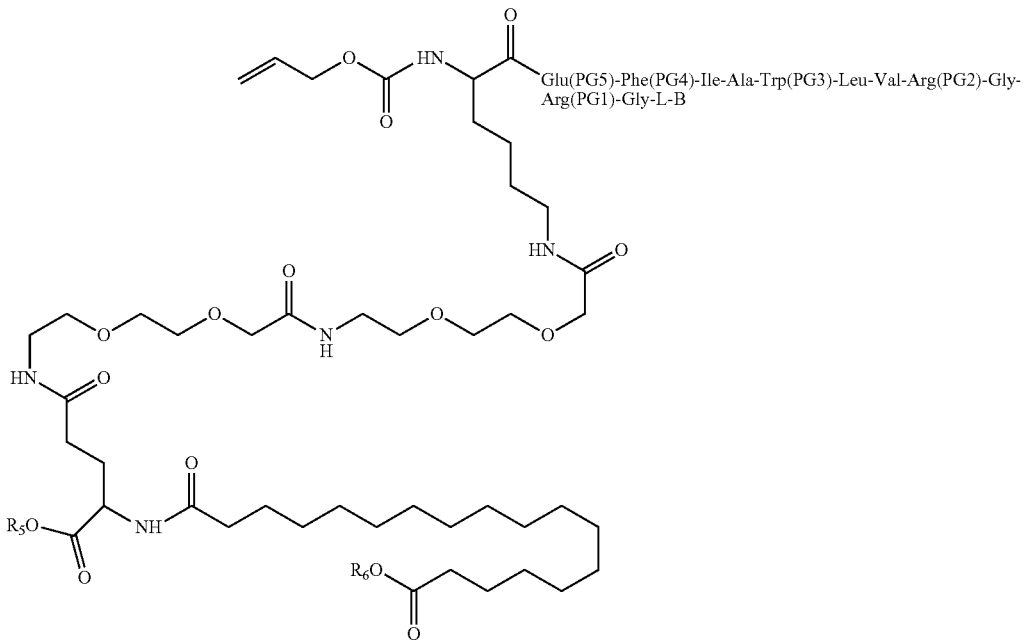

d) Removing the Alloc protecting group so as to expose a free N-terminal alpha amino group;
e) Coupling, by stepwise solid-phase peptide synthesis, the amino acid sequence $R_7$-His(PG19)-Aib-Glu(PG18)-Gly-Thr(PG17)-Phe(PG16)-Thr(PG15)-Ser(PG14)-Asp(PG13)-Val-Ser(PG12)-Ser(PG11)-Tyr(PG10)-Leu-Glu(PG9)-Gly-Gln(PG8)-Ala-Ala- to said free N-terminal alpha amino group so as to obtain a solid-phase bound semaglutide peptide, wherein: PG8 to PG19 independently are H or side chain protecting groups and are the same as or different from any of each other and/or any of PG1 to PG7, and $R_7$ is H or an amino protecting group, which may be the same as or different from $R_1$;
f) Cleaving the semaglutide peptide from the solid phase, typically, cleaving the semaglutide peptide from the solid phase and (concomitantly) cleaving the protecting groups from the semaglutide peptide (deprotection).

In one embodiment, step e) of the above method involves coupling, by stepwise solid-phase peptide synthesis, the amino acid sequence $R_7$-His(PG18)-Aib-Glu(PG17)-Gly-Thr(PG16)-Phe-Thr(PG15)-Ser(PG14)-Asp(PG13)-Val-Ser(PG12)-Ser(PG11)-Tyr(PG10)-Leu-Glu(PG9)-Gly-Gln(PG8)-Ala-Ala- to said free N-terminal alpha amino group so as to obtain a solid-phase bound semaglutide peptide, wherein: PG8 to PG18 independently are H or side chain protecting groups and are the same as or different from any of each other and/or any of PG1 to PG7, and R7 is H or an amino protecting group, which may be the same as or different from R1.

It will be understood that, as used herein, the term "semaglutide peptide" may also include salts thereof, in particular salts containing counterions resulting from agents used during conducting the methods of the present invention (e.g., resulting from protection groups, scavengers, cleaving agents or the like) or pharmaceutically acceptable salts.

The present invention further relates to solid-phase bound peptides, to peptides obtainable according to the methods of the present invention, and to pharmaceutical compositions comprising said peptides. The peptides produced according to the methods of the present invention are characterized by a specific and favorable impurity profile.

In general, several abbreviations and definitions are used throughout the present invention:

Abbreviations:
Alloc=Aloc=AOC, allyloxycarbonyl
Aib 2-aminoisobutyric acid
Boc t-butoxycarbonyl
DBU diazabicyclo[5.4.0]undec-7-ene
DCM dichloromethane
Dde 2-(4,4-dimethyl-2,6-dioxocyclohexylidene)ethyl
DEPBT 3-(diethoxy-phosphoryloxy)-3H-benzo [d][1,2,3] triazin-4-one
DIC diisopropylcarbodiimide
DIPEA diisopropylethylamine
Dmb 2,4-dimethoxybenzyl
DMF N,N-dimethylformamide
DTE dithioerythriol
DTT dithiothreitol
EDC 1-Ethyl-3-(3-dimethyl-aminopropyl)-carbodiimide
EDT ethanedithiol
Fmoc 9-fluorenylmethyloxycarbonyl
Fmoc-AEEAc-OH Fmoc-8-amino-3,6-dioxa-octanoic acid
HATU N-[(7-Aza-1H-benzotriazol-1-yl) (dimethylamino)-methylene]-N-methylmethanaminium hexafluorophosphate N-oxide
HBTU 2-(1H-benzotriazol-1-yl)-1,1,3,3-tetramethyluronium hexafluorophosphate
HFIP hexafluororisopropanol
Hmb 2-hydroxy-4-methoxybenzyl
HOBt hydroxybenzotriazole
HOSu N-Hydroxysuccinimide HPLC High Performance Liquid Chromatography
IPA isopropyl alcohol
ivDde 1-(4,4-dimethyl-2,6-dioxocyclohex-1-ylidene)isovaleryl
IPE diisopropyl ether
LPPS Liquid Phase Peptide Synthesis
Mtr 2,3,6-trimethyl-4-methoxybenzenesulfonyl
Mmt 4-methoxytrityl
Mtt 4-methyltrityl
MTBE methyl tert. butyl ether
NMP N-methylpyrrolidone
OMpe 3-methylpent-3-yl ester
OPp 2-phenyl isopropyl
OtBu t-butyl ester
Oxyma=OxymaPure®, cyano-hydroxyimino-acetic acid ethyl ester
Pbf 2,2,4,6,7-pentamethyldihydrobenzofuran-5-sulfonyl
Pmc 2,2,5,7,8-pentamethylchroman-6-sulfonyl
SPPS Solid Phase Peptide Synthesis
tBu tert. Butyl
TATU N-[(7-Aza-1H-benzotriazol-1-yl) (dimethylamino)-methylene]-N-methylmethanaminium tetrafluoroborate
TBTU (benzotriazolyl)tetramethyluronium tetrafluoroborate
TES triethylsilane
THF tetrahydrofuran
TIPS=TIS=triisopropylsilane
TFA trifluoroacetic acid
Trt trityl
UHPLC Ultra High Performance Liquid Chromatography Unless indicated otherwise, liquid mixtures are defined by volume percentages and volume ratios.

As used herein, the term "amino acid" refers to an organic acid—i.e. a compound containing at least one carboxyl group (—COOH)—, which further contains at least one amino group (—NH$_2$). Alpha amino acids (RCH(NH$_2$)COOH) are the building blocks, from which peptides and proteins are predominantly constructed. However, in particular artificial peptides may contain building blocks other than alpha amino acids. Alpha amino acids will be referred to interchangeably by either their full name (exemplified: alanine), 3-letter code according to WIPO Standard ST. 25 (e.g. Ala), or 1-letter code (e.g. A). As far as the enantiomeric form is not expressly specified, L-alpha amino acids are in general referred to. It should be noted, however, that the present invention can likewise be put to practice using D-alpha amino acids and other stereoisomers.

As used herein, the term "peptide" and "polypeptide" may be understood interchangeably and relates to compounds, where at least two amino acids are covalently linked by an amide bond between a carboxyl group of one amino acid moiety and the amino group of the amino acid moiety. Typically, this bond is between the carboxyl group of a first alpha amino acid and the (alpha) amino group of a second alpha amino acid and is referred to as "peptide bond". Unless indicated otherwise, peptide sequences are indicated herein starting with the N-terminus (left) and ending with the C-terminus (right). Table 1 illustrates different notations, which are equivalent and will be used interchangeably throughout this document.

TABLE 1

| Notation of peptides | |
|---|---|
| Notation | Explanation |
| H-Gly-Leu-Ala-OH | This notation stresses that the N-terminal amino group ("H") and C-terminal carboxyl ("OH") group are not modified. |
| Gly-Leu-Ala | Terminal groups are only expressly stated if they are modified. |
| GLA | 1-letter code. Terminal groups are only expressly stated if they are modified. |
| Glycyl-L-leucyl-L-alanine | "written out in full" |

The following notation will be used for derivatives of alpha amino acids: Substituents at the alpha amino group (N$^\alpha$) are indicated to the left of the amino acid symbol and separated by a hyphen, substituents at the alpha carboxy group are indicated to the right of the amino acid symbol and separated by a hyphen, substituents at the side chain are indicated in brackets immediately to the right of the amino acid symbol. For unmodified alpha-amino acids, the substituent at the alpha amino group (N$\alpha$) is a proton (H—) and the substituent at the alpha carboxy group is a hydroxyl (—OH)

For branched dipeptides, the above notation is adhered to in a nested format. For example, Fmoc-Lys(Boc-Glu-OtBu)-OH refers to a Lys derivative with a Fmoc protected alpha amino group and a free alpha carboxyl group, whose side chain is substituted with a glutamyl moiety having a Boc protected alpha amino group and an OtBu protected carboxyl group. The glutamyl moiety forms an amide bond to the Lys side chain via its gamma carboxyl group.

The analogous notation is used for substituted amino acids, which are part of a peptide. For example, Aaa1-Aaa2-Lys(AEEAc-Alloc)-Aaa4-Aaa5 refers to a branched pentapeptide, where the Lys side chain at position 3 is substituted with a amide bonded 8-amino-3,6-dioxa-octanoic acid moiety having an Alloc protected alpha amino group. Hence, said amide bond is between the Lys' epsilon amino group and the carboxyl group of AEEAc.

As a further example of a substituted amino acid, which is part of a peptide, the expression -Lys(AEEAc-AEEAc-g-Glu-17-carboxyheptadecanoyl)- refers to a structure of the formula 1 below.

Formula 1

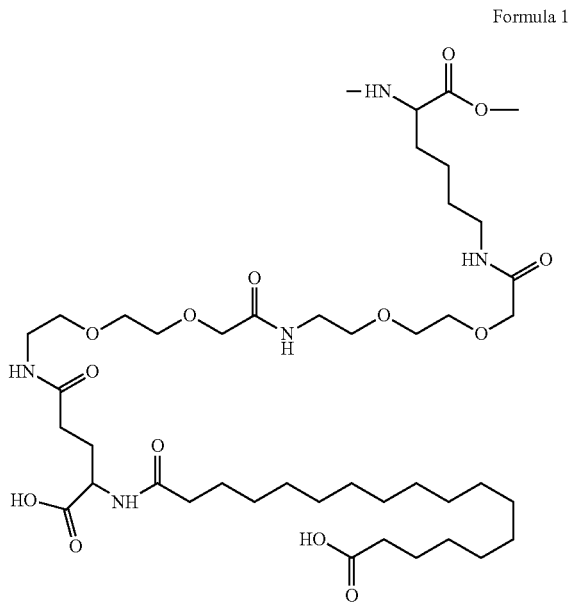 [SMILES: CNC(CCCCNC(=O)COCCOCCNC(=O)COCCOCCNC(=O)CCC(NC(=O)CCCCCCCCCCCCCCCCC(=O)O)C(=O)O)C(=O)OC]

Semaglutide is a peptide of SEQ ID NO: 1, wherein the lysine in position 20 (26) carries a substituent as depicted in formula 1 above. Hence, semaglutide may be referred to as H-His-Aib-Glu-Gly-Thr-Phe-Thr-Ser-Asp-Val-Ser-Ser-Tyr-Leu-Glu-Gly-Gln-Ala-Ala-Lys(AEEAc-AEEAc-γ-Glu-17-carboxyheptadecanoyl)-Glu-Phe-Ile-Ala-Trp-Leu-Val-Arg-Gly-Arg-Gly-OH.

The person skilled in the art will notice that in a polar environment, in particular in an aqueous environment, the peptide strand of the peptide of SEQ ID NO: 1 or of any other glucagon-like peptide may form a salt such as, e.g., by means of binding protons or other cations and/or anions, releasing protons or other cations and/or anions at the termini and/or a some of the amino acid side chains. The same applies to the substituent at the lysine side chain as depicted in formula 1.

It will be understood by a person skilled in the art that a semaglutide peptide as used herein may optionally bear any counter ions known in the art, such as anions or cations, such as e.g., chloride ions, acetate ions, carbonate ions, hydrocarbonate ions, sodium ions, potassium ions, magnesium ions, any ions of a cleavage solution (e.g., TFA ions, bromide ions, perchlorate ions, ammonium ions) and/or cations or anions of residuals of protecting groups. Further, a peptide may optionally be covalently or non-covalently associated to traces of one or more scavengers, such as, e.g., triisopropylsilane (TIS), dithiothreitol (DTT), anisole, thioanisole or 1,2-ethanedithiol.

Preferably, a semaglutide peptide as used herein is free of any protecting groups and has no other modifications at amino acid side chains except the moiety of Lys[20]. Accordingly, the semaglutide peptide is preferably the fully unprotected peptide, which is preferably not further modified.

Alternatively, the N-terminus of the peptide of formula I may be modified (e.g, acylated (e.g., acetylated)). Alternatively or additionally, the C-terminus may be modified (e.g., amidated).

Alternatively or additionally, one or more amino acid moiety side chains may be conjugated with a fluorophore. Optionally, the peptide of formula I may also be labeled radioactively (e.g., by $^3$H, $^{32}$P, $^{35}$S, $^{14}$C, $^{99m}$Tc or lanthanides (e.g., $^{64}$Gd)) or may be labelled with a spin label, such as one or more heavy isotopes, e.g., $^{13}$C, detectable by Nuclear Magnetic Resonance (NMR).

The peptide synthesized by means of the present invention will typically consist of natural L-alpha amino acids. However, alternatively, the peptide may also comprise one or more non-natural amino acid(s) such as, e.g., D-alpha amino acid(s), beta amino acid(s), methylated amino acid(s) (e.g., N-methylated amino acid(s)) or may even consist of such.

The term "glucagon-like peptide" or GLP as used herein refers to the homologous peptides derived from the GCG gene (HGNC:4191), the extendins and analogs thereof as well as derivatives of any of the foregoing.

The terms "glucagon-like peptide 1 analogs" and "GLP-1 analogs" are used herein interchangeably. As used herein, they relate to peptides capable of binding to the GLP-1 receptor. Derivatives and analogs of GLP-1 (7-37) and of extendins 4 (1-39) such as Exenatide, Lixisenatide, and Liraglutide are preferred GLP-1 analogs. Exemplarily, a GLP-1 analog may comprise a polypeptide strand having at least 80%, 90% or 95% homology to the sequence of human GLP-1 (7-37), and, optionally, also a modification in the lysine moiety homolog to Lys[20] (Lys 28) of human GLP-1 (7-37). Homology as used herein is preferably sequence homology. As used herein, sequence homology may refer to any definition of sequence homology known in the art. In particular, sequence homology may be understood as sequence homology determined by BLAST (Basic Local Alignment Search Tool) of the National Center for Biotechnology Information (NCBI) in the version of the filing date of the present application.

The term "analogs" or "analogs" as used herein is used for peptides whose sequence is derived from a first peptide sequence by replacement of up to 50% of the amino acid moieties, and/or by deletion of up to 10% of the amino acid moieties of said first peptide sequence, and/or by addition of up to 10 amino acid moieties. Preferred analogs are derived from a first peptide sequence by replacement of up to 20% of the amino acid moieties, and/or by deletion of up to 10% of the amino acid moieties of said first peptide sequence, and/or by addition of up to 10 amino acid moieties.

The term "derivative" or "derivatives" as used herein refers to a compound which can be obtained from a first compound by a chemical reaction. As a result, a derivative may differ from the first compound by the presence or absence of substituents. For example, amino acid derivatives for use in SPPS usually differ from the amino acid they are derived from at least by the presence of an amino protecting group. Depending on the nature of the specific amino acid, standard amino acid derivatives usually further comprise side chain protecting groups.

The term "protecting group" as used herein may be understood in the broadest sense as a group which is introduced into a molecule by chemical modification of a functional group to block said group from reaction in subsequent process steps, e.g. to prevent side reactions of the amino acid side chains.

Examples of amino protecting groups are the Boc and Fmoc groups, examples of carboxylic acid protecting groups are unreactive esters such as Methyl esters, Benzyl esters, or tert. Butyl esters.

Typically, peptide synthesis (based on SPPS and LPPS) involves the use of various protecting groups and activated esters. Therefore, according to one embodiment of the present invention, various protecting groups and activated esters may be used during the synthesis of a peptide, in particular of a semaglutide peptide.

In the context of the present invention, the term "activated ester" may be understood in the broadest sense as an ester, which is suitable to spontaneously react with an amino group. Examples of activated esters are p-nitrophenyl, pentafluorophenyl and succinimido esters.

At least one, preferably all of the steps a), c), and e) of the method according to the present invention are preferably carried out by Solid Phase Peptide Synthesis (SPPS). In SPPS, a precursor peptide is synthesized on a resin, i.e., on a "solid phase", most typically a bead-like structure which can be easily separated from liquid phase by filtration. Subsequent to synthesis of the resin-bound peptide, the peptide is released from the resin and protective groups are removed.

As used herein, the terms "resin" and "[resin]" may be understood in the broadest sense as a bead-like structure usable for SPPS. The terms "resin", "solid phase", "solid support", and "support" are used exchangeably herein.

SPPS is commonly carried out on gel phase rather than solid phase supports. Suitable resins may be based on polystyrene, polystyrene-PEG composites, PEG, PEGA, cross-linked ethoxylate acrylate (CLEAR), polyamides, polydimethylacrylamide, or any other support with the desired physical and chemical properties. Resins based on beaded polystyrene with 1% divinylbenzene are among the routinely used supports, typically having a size distribution of 200-400 mesh or 100-200 mesh.

As used herein, the term "linker" is used to refer to bifunctional molecules anchoring the growing peptide to the insoluble carrier. Linkers may be coupled to any carrier suitable for SPPS.

The C-terminal Fmoc amino acid may be coupled to the linker yielding the so-called handle which can be purified before loading the polymer. High loads regardless of the bulkiness of the amino acid are obtained by coupling these handles.

Linkers suitable for use with the present invention include, but are not limited to:
4-hydroxybenzylalcohol (Wang linker)
Sasrin linker
CTC Amido-methyl linker
CTC linker
(4-(3-hydroxy-3-methyl-butyl)-phenoxy)-acetic acid
Fmoc-2,4-dimethoxy-4'-(carboxymethyloxy)-benzhydrylamine (Rink Amide Linker)
Fmoc-4-methoxy-4'-(-carboxypropyloxy)-benzhydrylamine.
4-Formyl-3-methoxy-phenoxyacetic acid
2-Hydroxy-5-dibenzosuberone
4-Hydroxymethylbenzoic acid (HMBA)
4-Hydroxymethyl-3-methoxy-phenoxyacetic
4-Hydroxymethyl-phenoxyacetic acid (HMP linker)
4-(Fmoc-hydrazino)-benzoic acid
4(4-(1-hydroxyethyl)-2-methoxy-5-nitrophenoxy)-butyric acid
Fmoc-Suberol (5-Fmoc-amino-2-carboxymethoxy-10,11-dihydro-5H-dibenzo[a,d]cycloheptene) (Ramage linker)

Polystyrene based 4-Alkoxybenzyl alcohol (Wang) resin, polymeric diphenyldiazomethane (PDDM) resin, 4-(2',4'-Dimethoxyphenyl-Fmoc-aminomethyl)-phenoxymethyl-polystyrene (Rink) resin, 2-Methoxy-4-alkoxybenzyl alcohol (Sasrin) resin, and especially 2-Chlorotrityl chloride (CTC) resin are particularly suitable for use with the methods of the present invention and are commercially available from suppliers such as Sigma-Aldrich, Bachem and EMD Millipore. However, any other resin suitable for SPPS may be used.

The skilled person will immediately recognize that, for use with the present invention, a suitable linker structure is preferably orthogonal to the amino protecting groups Alloc and $R_1$. This allows for removal of said protecting groups, while keeping the peptide immobilized on the solid phase.

As used herein, two moieties comprised in a precursor peptide are considered "orthogonal", if the first moiety can be removed from said precursor peptide essentially without affecting the second moiety. As a non-limiting example, the protecting groups Alloc and Fmoc are orthogonal to each other. As a further non-limiting example, each of the Alloc and Fmoc protecting groups is orthogonal to the side chain protecting groups Pbf, OtBu, tBu, OMpe, Trt, Mtt, Mmt, Boc, and to the linker structures of Wang resin, CTC resin, and Sasrin resin.

As an alternative to immobilization via the C-terminal carboxyl group, the peptide may also be conjugated to the resin via a side chain of a (preferably terminal) amino acid.

The person skilled in the art will be aware of a large variety of SPPS methods. In general, any type of SPPS may be used in the context of the present invention. Various types of equipment can be used for SPPS. Manual, semi-automated and automated synthesizers for either batchwise or continuous flow SPPS are available. For any given equipment, the resin may be chosen properly so as to meet the mechanical requirements imposed by the equipment.

The person skilled in the art is well aware of the fact that resin load may influence effectivity in SPPS, in particular in industrial SPPS. This may have particular impact when dealing with long, aggregation-prone peptide sequences such as the glucagon-like peptides: On one side, process efficiency increases with increasing resin load. On the other side, it is essential to reduce on-resin precipitation by reducing resin load. Hence, a delicate balance may be met and the optimal resin load can be established by routine experimentation for any given SPPS protocol. Resin load can be varied, e.g., either by using resins for which different substitution degrees are commercially available, or by coupling the second amino acid in molar deficit relative to the first amino acid, and subsequently acetylating, i.e. blocking, unreacted first amino acids. Likewise, the first amino acid may be coupled in molar deficit to the resin, followed by a blocking step.

In preferred embodiments of the present invention, a resin load in the range of around 0.2 mmol/g to around 0.9 mmol/g is used, for example around 0.2 mmol/g, 0.3 mmol/g, 0.4 mmol/g, 0.5 mol/g, 0.6 mmol/g, 0.7 mmol/g, 0.8 mmol/g, or 0.9 mmol/g. In this context, it may be noted that, during SPPS, the swelling and shrinking of the resin in the various solvents used can lead to considerable fluctuations of resin volume and hence peptide concentration on the resin.

The term $R_1$ is used throughout the present application to refer to an amino protecting group. Preferably, $R_1$ is an amino protecting group, which is orthogonal to Alloc. In one embodiment, $R_1$ is selected from the group consisting of 9-fluorenyl-methoxycarbonyl (Fmoc), t-butyloxycarbonyl (Boc), 4-methyltrityl (Mtt), 4-methoxytrityl (Mmt), or trityl (Trt). In a most preferred embodiment, R1 is a 9-fluorenyl-methoxycarbonyl (Fmoc) group.

The steps a), c), and e) of the method according to the present invention are therefore preferably carried out by Fmoc-SPPS. Hence, the cycles of chain elongation preferentially involve the coupling of a building block, which comprises a free carboxyl group and/or an activated ester of a carboxyl group, a Fmoc-protected amino group, and optionally further protecting groups. Optionally, the building block used in the last chain elongation reaction of steps c) and/or e) may lack an Fmoc-protected amino group.

As used herein, the term "building block" refers to a moiety, which is used as one educt of the chain elongation reaction, and which is incorporated at least in part into the growing solid phase bound molecule during said chain elongation reaction. Hence, the building blocks used with the present invention typically comprise a free carboxyl group and/or an activated ester of a carboxyl group, a $R_1$-protected amino group, and optionally further protecting groups. When used in the last chain elongation reaction, the building blocks may lack a $R_1$-protected amino group.

Therefore, the methods of the present invention comprise performing solid phase peptide synthesis using building blocks, which comprise a free carboxyl group, an R1 protected amino group, and optionally further protecting groups, and wherein the steps of:

i) coupling a building block, which comprises an R1 protected amino group, to a free amino group generated in a previous step; and ii) removal of R1 to expose a free amino group are carried out in repeated cycles.

Typical building blocks for use with embodiments of the present invention include $R_1$ protected AEEAc-OH, carboxylic acids, dicarboxylic acids, mono-esters of dicarboxylic acids, $R_1$ protected amino acid derivatives, and $R_1$ protected dipeptide derivatives such as $R_1$ protected pseudoproline dipeptide derivatives.

In particular preferred are Fmoc-AEEAc-OH, Alloc-Lys (Fmoc)-OH, carboxylic acids, dicarboxylic acids, mono-esters of dicarboxylic acids, Fmoc amino acid derivatives, and Fmoc dipeptide derivatives.

In one embodiment of the present invention, step c) is performed by stepwise solid-phase synthesis using Fmoc-AEEAc-OH, Fmoc-Glu-OtBu, and octadecanedioic acid or octadecanedioic acid mono-t-butyl ester as building blocks.

In one embodiment of the present invention, each building building block used in steps a) and/or e) is selected independently from the group consisting of:

1) derivatives of alpha-amino acids, wherein the alpha amino group is protected by Fmoc, optionally further wherein the amino acid side chain carries a protecting group; and/or 2) Alloc-Lys(Fmoc)-OH; and/or 3) dipeptide derivatives, which comprise an Fmoc or Boc protected amino group, preferably an Fmoc or Boc protected N-terminal alpha amino group, optionally further wherein at least one amino acid side chain carries a protecting group.

In one embodiment of the present invention, at least one building block is selected from the group consisting of:

1) amino acid derivatives, which comprise an $R_1$ protected amino group, preferably derivatives of alpha-amino acids, wherein the alpha amino group is protected by $R_1$ and the side chain and/or the alpha carboxyl group optionally carry protecting groups; and/or 2) dipeptide derivatives, which comprise an $R_1$ protected amino group, preferably an $R_1$ protected N-terminal alpha amino group; and/or 3) derivatives of 8-amino-3,6-dioxa-octanoic acid (H-AEEAc-OH), which comprise an $R_1$ protected amino group, preferably $R_1$-AEEAc-OH.

Pseudoproline dipeptide derivatives are preferred dipeptide derivatives in the context of the present application.

In one embodiment of the present invention, a building block, which does not contain an amino group, is used in the last chain elongation step of step c) and/or of step e).

In one embodiment of the present invention, the building block used in the last chain elongation step of step c) and/or step e) is a carboxylic or dicarboxylic acid.

Suitable Fmoc amino acid derivatives for use with embodiments of the present invention comprise the standard compound Fmoc-Ala-OH, Fmoc-Arg(Pbf)-OH, Fmoc-Arg (Pmc)-OH, Fmoc-Asn(Trt)-OH, Fmoc-Asn(Mtt)-OH, Fmoc-Asp(OtBu)-OH, Fmoc-Asp(OMpe)-OH, Fmoc-Cys (Trt)-OH, Fmoc-Cys(Mmt)-OH, Fmoc-Gly-OH, Fmoc-Gln (Mtt)-OH, Fmoc-Gln(Trt)-OH, Fmoc-Glu(OtBu)-OH, Fmoc-His(1-Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp (Boc)-OH, Fmoc-Tyr(tBu)-OH, and Fmoc-Val-OH, which are commercially available from various sources.

It should be noted that the use of non-natural amino acid derivatives such as Aib (α-aminoisobutyric acid), Nle (norleucine), or Orn (ornithine) in the synthesis peptides is likewise encompassed by the methods of the present invention. In a preferred embodiment, the amino acid derivatives Fmoc-Aib-OH, Fmoc-Ala-OH, Fmoc-Arg(Pbf)-OH, Fmoc-Asp(OtBu)-OH, Fmoc-Asp(OMpe)-OH, Fmoc-Gly-OH, Fmoc-Gln(Trt)-OH, Fmoc-Glu(OtBu)-OH, Boc-His(Boc)-OH, Fmoc-His(1-Trt)-OH Fmoc-Ile-OH, Fmoc-Leu-OH, Fmoc-Phe-OH, Fmoc-Ser(tBu)-OH, Fmoc-Thr(tBu)-OH, Fmoc-Trp(Boc)-OH, Fmoc-Tyr(tBu)-OH, and Fmoc-Val-OH are used. The use of Fmoc-Trp(Boc)-OH with Fmoc-Arg(Pbf)-OH allows to suppress sulfonyl modification of tryptophan moieties by cationic species during peptide cleavage from the resin. However, as TFA cleavage from the resin may result in formation of side products such as carbamates, it can be advantageous to subject the crude peptide to a decarboxylation reaction. This may, exemplarily, be achieved by subjecting the crude peptide to a high pH treatment such as, e.g., a pH of at least 7.2, at least 8.0, at least 8.5, at least 9, at least 9.5, at least 10, at least 10.5, at least 11, or at least 11.5. Alternatively or additionally, decarboxylation reactions may be performed in mildly acid conditions such as, e.g. a pH of 6.0 to 7.0, pH of 5.5. to 6.5, or a pH of 5.0 to 6.0. Optionally, said treatments may be accompanied by a heat treatment, e.g., at a temperature of 30-70° C., for example at 30° C., 35° C., 40° C., 45° C., 50° C., 55° C., 60° C., 65° C., or 70° C.

The person skilled in the art is well-aware of SPPS methods based on an Fmoc synthesis protocol. Each cycle of building block addition to the resin typically starts with Fmoc cleavage, i.e., removal of the Fmoc protecting group from the resin-bound peptide chain. This is achieved by incubating the peptide resin with a base in a solvent capable of swelling the resin and dissolving the reagents.

Popular bases for this purpose comprise, e.g., secondary amines such as piperidine and 4-methyl piperidine. Suitable solvents comprise, e.g., DMF, NMP, dimethyl sulfoxide, dichlormethane, tetrahydrofuran, acetonitrile, toluol, and mixtures thereof. The reaction is commonly carried out at ambient temperature, e.g. within a temperature range of 15-30° C. Usually, the base-labile and acid-stable Fmoc is split off by a short treatment (2 to 15 minutes, e.g. 2, 3, 4, 5, 6, 7, 8, 9, 10, 11, 12, 13, 14, or 15 minutes) with 5-50%, preferably 20%, piperidine in DMF (v/v).

Where necessary, this treatment is repeated and/or slightly prolonged (7 to 30 minutes, e.g. 7, 8, 9, 10, 11, 12, 13, 14, 15, 16, 17, 18, 19, 20, 21, 22, 23, 24, 25, 26, 27, 28, 29, or 30 minutes). For synthesis of large peptides with difficult-to-cleave stretches, the duration of Fmoc cleavage as well as the number of repetitions may be gradually increased. For instance, the cleavage time may be 15-75 minutes, e.g. 15, 30, 45, 60, or 75 minutes, and the cleavage may be repeated up to 8 times, e.g. 2, 3, 4, 5, 6, 7, or 8 times. Moreover, the temperature may be increased, e.g. to a temperature between 30° C. and 45° C. Under those conditions, complete deblocking is achieved in most cases. Additionally or alternatively, the reagent used for Fmoc cleavage may be varied.

It has been found that even slight variations of the reagent may considerably accelerate the cleavage, e.g. the use of: 1 to 5% DBU in DMF, 20% piperidine and 1-5% DBU in DMF, 20% piperidine in NMP, or 20% piperidine in DMF at 45° C. Moreover, acceleration of the cleavage reaction may be achieved by microwave treatment. On the other side, the nature of the peptide may render the use of milder treatments advantageous. Particular mild cleavage conditions are, e.g., 0.1 M HOBt plus 20% piperidine in DMF, 50% morpholine in DMF, 2% HOBt plus 2% hexamethyleneimine plus 25% N-methylpyrrolidine in 50% DMSO in NMP. The skilled person will routinely optimize and control Fmoc cleavage conditions at each step of the synthesis.

In a preferred embodiment, the Fmoc protecting group is cleaved off the growing peptide chain conjugated to the solid phase using a mixture selected from the group consisting of 5-50% (v/v) piperidine or 4-methyl piperidine in N,N-dimethylformamide (DMF), 5-50% (v/v) piperidine or 4-methyl piperidine in N-methylpyrrolidone (NMP), 1-5% (v/v) diazabicyclo[5.4.0]undec-7-ene (DBU) in DMF, and 50% (v/v) morpholine in DMF.

The cleavage reagent is typically washed out carefully after Fmoc-removal. DMF and optionally IPA are used for washing until neutral pH. To ensure complete base removal, it may be advantageous to add small amounts of HOBt in in later washing cycles.

The above considerations are likewise applicable to the step b) of the methods according to the present invention, i.e. to the step of removing the Fmoc/$R_1$ group from the compound of formula (i) or formula (vii).

The coupling of a building block, usually an amino acid derivative, to the (peptide) resin, i.e. the elongation step, is one of the central steps of the SPPS cycle. Rate and yield of the reaction may be influenced by various parameters such as the choice of solvent, the steric hindrance, and the reactivity of the activated carboxylic acid. The solvent may not only determine the swelling of the precursor peptide-resin and may thus influence the accessibility of the reactive sites; it may also directly affect the kinetics of the coupling reaction. Suitable solvents are capable of swelling the resin and dissolving the reagents and comprise, e.g., DMF, NMP, dimethyl sulfoxide, dichlormethane, tetrahydrofuran, acetonitrile, toluol, and mixtures thereof. The steric hindrance is determined by the nature of the amino acid side chains and their protecting groups. The reactivity of the activated carboxylic acid determines the acylation rate, as well as the extent of side reactions, such as racemization. Depending on the synthesis strategy chosen, peptide derivatives such as pseudoproline dipeptide derivatives, di- or tripeptide derivatives, or branched dipeptide derivatives may be used in lieu of single amino acid derivatives.

In certain embodiments of the present invention, building block activation is carried out in DMF as a solvent, i.e. the building block, a coupling reagent and optionally an additive are dissolved in DMF and mixed. DIC may be used as coupling reagent in combination with either OxymaPure® or HOBt as an additive. In the alternative, TBTU or DEPBT may be used to convert the Fmoc amino acid into an active OBt or ODhbt ester in the presence of a base, preferably DIPEA. Further alternatives comprise TATU plus DIPEA, HBTU plus DIPEA, and HATU plus DIPEA. The building block of choice is pre-activated by incubation with the above reagents for 1-30 min, e.g. for 2, 3, 4, 5, 6, 7, 8, 9, 10, . . . , 28, 29, or 30 min before addition to the resin.

The coupling reaction is allowed to proceed for 1 to 74 h, e.g. for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, . . . , 71, 72, 73, or 74 h. The building block may be used in a 0.4-3 molar ratio relative to the amount of resin-bound amine groups, e.g. at a molar ratio of 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In order to achieve complete coupling, it may be advantageous to add a second portion of activating agent or base to the reaction mixture after some time, e.g. after 10, 20, 30, 40, or 60 min. The pre-activation and coupling steps are commonly carried out at room temperature, but may also be performed at other temperatures. It may be advantageous to perform one or more re-coupling steps in order to achieve near to complete conversion of amino groups.

In other embodiments of the invention, amino acid activation is carried out in a solvent consisting of NMP, dimethyl sulfoxide, dichlormethane, tetrahydrofuran, acetonitrile, toluol, and mixtures thereof, optionally with DMF.

In a preferred embodiment, steps a), c), and e) of a method according to the present invention comprises Fmoc-based Solid Phase Peptide Synthesis (SPPS) using suitably protected amino acid derivatives or dipeptide derivatives, wherein said protected amino acid derivatives or dipeptide derivatives are activated by means of one or more coupling reagent/additive mixtures selected for each step independently from the group consisting of
  (A) TBTU/DIPEA;
  (B) DIC/OximaPure® (cyano-hydroxyimino-acetic acid ethyl ester);
  (C) DEPBT/DIPEA; and
  (D) DIC/HOBt.

In a preferred embodiment, at least one, preferably all, of steps a), c), and e) of a method according to the present invention comprises/comprise activating the building blocks used by means of one or more coupling reagent mixtures comprising reagents selected for each coupling reaction independently from the group consisting of:
  (A) (benzotriazolyl)tetramethyluronium tetrafluoroborate (TBTU) plus diisopropylethylamine (DIPEA);
  (B) diisopropylcarbodiimide (DIC) plus cyano-hydroxyimino-acetic acid ethyl ester (Oxyma);
  (C) 3-(diethoxy-phosphoryloxy)-3H-benzo[d][1,2,3]triazin-4-one (DEPBT) plus DIPEA;
  (D) DIC plus hydroxybenzotriazole (HOBt);
  (E) N-[(7-Aza-1H-benzotriazol-1-yl) (dimethylamino)-methylene]-N-methylmethanaminium tetrafluoroborate N-oxide (TATU) plus DIPEA;
  (F) 2-(1H-benzotriazol-1-yl)-1,1,3,3-tetramethyluronium hexafluorophosphate (HBTU) plus DIPEA; and
  (G) N-[(7-Aza-1H-benzotriazol-1-yl) (dimethylamino)-methylene]-N-methylmethanaminium hexafluorophosphate N-oxide (HATU) plus DIPEA.

The coupling of His derivatives is preferably carried out so as to avoid racemization. This side reaction can be reduced by three different approaches: 1) blocking of the N3 of the imidazole ring, 2) blocking of the N1 of the imidazole ring by electron withdrawing groups such as Boc or Tos, and 3) optimization of coupling conditions when using Fmoc-His(1-Trit)-OH. It is therefore recommended to use Fmoc-His(1-Trit)-OH, Boc-His(1-Trt)-OH, or Boc-His(Boc)-OH, most preferably Boc-His(Boc)-OH, in combination with DEPBT/DIPEA to introduce an N-terminal His. Further options include the use of dipeptide derivatives such as Fmoc-His(1-Trit)-Aib-OH, Boc-His(1-Trit)-Aib-OH, Boc-His(Boc)-Aib-OH, or Fmoc-His(Boc)-Aib-OH. Sill further options include the use of dipeptide derivatives such as Fmoc-His(1-Trit)-Ala-OH, Boc-His(1-Trit)-Ala-OH, Boc-His(Boc)-Ala-OH, or Fmoc-His(Boc)-Ala-OH.

Therefore, in a preferred embodiment, the N-terminal histidine moiety is introduced into the precursor peptide conjugated to the solid phase using an amino acid derivative selected from the group consisting of Boc-His(Boc)-OH, Boc-His(1-Trt)-OH, and Fmoc-His(1-Trt)-OH and the coupling reagent/additive mixture DEPBT/DIPEA. Alternatively, suitably protected His-Aib-Dipeptides may be used as building blocks.

Capping may be performed to block unreacted amines from peptide bond formation in the following steps of synthesis, i.e., to avoid the formation of deletion variants of the sequence to be synthesized.

This may be achieved by a short treatment of the peptide resin with a large excess of a highly reactive unhindered acid derivative, e.g. N-hydroxysuccinimide, acetic anhydride or benzoyl chloride, and a base, e.g. pyridine, collidine, or DIPEA, optionally in the presence of an additive such as OxymaPure® or HOBt. Capping will typically yield a truncated sequence, which generally differs considerably from the final peptide and can be readily separated. Preferably, systematic double coupling is followed by capping. At the end of the capping step, the reagents are typically filtered off and the resin is carefully washed, e.g. with DMF and optionally IPA, before proceeding to the next deprotection step.

Preferably, on-resin aggregation of the peptide, e.g. of semaglutide, is prevented during SPPS.

In particular glucagon-like peptides such as semaglutide intrinsically tend to aggregate, which represents an additional challenge for their efficient synthesis.

Stepwise Fmoc-SPPS may become comparably difficult or even fail as soon as the resin-bound peptide aggregates.

There are many possible options to mitigate such aggregation, including control of resin load by control of coupling density, control of resin shrinking during washing steps, addition of solvents such as DMSO, addition of chaotropic salts, addition of nonionic detergents and of ethylene carbonate, performing the coupling reaction at elevated temperature/under microwave treatment, and sonication of the coupling reaction mixture.

Further possible measures include introduction of at least one O-isoacyl peptide bond to serine or threonine, introduction of at least one pseudo proline dipeptide, or N-alkylation of at least one peptide bond by 2-hydroxy-4-methoxybenzyl (Hmb) or 2,4-dimethoxybenzyl (Dmb) moieties. Accordingly, at least one dipeptide derivative comprising a 0-isoacyl peptide bond such as Boc-Ser(Val-Fmoc)-OH or Boc-Thr(Gly-Fmoc)-OH may be used for this purpose. Alternatively or additionally, at least one dipeptide with an N-alkylated peptide bond such as Fmoc-Glu(OtBu)-(Dmb)Gly-OH and Fmoc-Ala-(Dmb)Ala-OH may be used.

It has surprisingly been found that the use of at least one Fmoc pseudoproline dipeptide advantageously suppresses peptide aggregation and hence the formation of by-products due to inefficient synthesis. Preferably, the pseudoproline dipeptide is introduced at a position corresponding to or identical with a position selected from $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of SEQ ID NO: 1.

The term "pseudoproline dipeptides" as used herein refers to temporary proline mimics, which can be readily obtained from Ser and Thr by oxazolidine formation and from Cys by thiazolidine formation. The person skilled in the art is well-aware of such pseudoproline dipeptides. These dipeptides are one possible option to mitigate on-resin aggregation during SPPS. The 2,2-dimethyloxazolidines (Psi(Me,Me)pro) are smoothly cleaved by TFA and thus particularly suitable for Fmoc-SPPS. Hence, in particular Fmoc-Gly-Thr(Psi(Me,Me)pro)-OH, Fmoc-Phe-Thr(Psi(Me,Me)pro)-OH, Fmoc-Thr(tBu)-Ser(Psi(Me,Me)pro)-OH, Fmoc-Val-Ser(Psi(Me,Me)pro)-OH, and/or Fmoc-Ser(tBu)-Ser(Psi(Me,Me)pro)-OH may be used.

Thus, the introduction of a pseudoproline moiety results in the provision of a solid-phase conjugated glucagon like peptide, preferably a solid-phase conjugated semaglutide, which is characterized by a reduced percentage of related impurities. A variety of pseudoproline dipeptide derivatives are known by the person skilled in the art (cf., brochure "Pseudoproline Dipeptides Bachem—Pioneering Partner for Peptides", published by Global Marketing, Bachem Group, November 2015). Therefore, in a preferred embodiment, one or more pseudoproline dipeptides are introduced at a position selected from the group consisting of $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of formula I.

In a particularly preferred embodiment, one or more pseudoproline dipeptide derivatives selected from the group consisting of Fmoc-Gly-Thr(Psi(Me,Me)pro)-OH, Fmoc-Phe-Thr(Psi(Me,Me)pro)-OH, Fmoc-Thr(tBu)-Ser(Psi(Me,Me)pro)-OH, Fmoc-Val-Ser(Psi(Me,Me)pro)-OH, and Fmoc-Ser(tBu)-Ser(Psi(Me,Me)pro)-OH is/are used.

According to a preferred embodiment, one or more pseudoproline dipeptide/s is/are introduced at a position identical with or corresponding to a position selected from the group consisting of $Gly^4$-$Thr^5$, $Phe^6$-$Thr^7$, or $Thr^7$-$Ser^8$ of the peptide of formula I. Preferably, a single pseudoproline dipeptide is introduced at a position corresponding to or identical with $Thr^7$-$Ser^8$ of the peptide of SEQ ID NO: 1.

In another preferred embodiment, a single pseudoproline dipeptide is introduced at a position corresponding to or identical with $Phe^6$-$Thr^7$ of the peptide of SEQ ID NO: 1. In a particularly preferred embodiment, one or more pseudoproline dipeptide/s selected from the group consisting of Fmoc-Gly-Thr(Psi(Me,Me)pro)-OH, Fmoc-Phe-Thr(Psi(Me,Me)pro)-OH, or Fmoc-Thr(tBu)-Ser(Psi(Me,Me)pro)-OH are used.

According to a preferred embodiment, the only pseudoproline dipeptide/s introduced is/are located at positions identical with or corresponding to a position selected from the group consisting of $Gly^4$-$Thr^5$, $Phe^6$-$Thr^7$, or $Thr^7$-$Ser^8$ of the peptide of SEQ ID NO: 1.

In a particularly preferred embodiment, the only pseudoproline dipeptide/s introduced is/are selected from the group consisting of Fmoc-Gly-Thr(Psi(Me,Me)pro)-OH, Fmoc-Phe-Thr(Psi(Me,Me)pro)-OH, or Fmoc-Thr(tBu)-Ser(Psi(Me,Me)pro)-OH.

According to a preferred embodiment, a single pseudoproline dipeptide is introduced at a position identical with or corresponding to a position selected from the group consisting of $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of SEQ ID NO: 1, preferably selected from the group consisting of $Gly^4$-$Thr^5$, $Phe^6$-$Thr^7$, and $Thr^7$-$Ser^8$ of the peptide of SEQ ID NO: 1. In a particularly preferred embodiment, a single pseudoproline dipeptide selected from the group consisting of Fmoc-Gly-Thr(Psi(Me,Me)pro)-OH, Fmoc-Phe-Thr(Psi(Me,Me)pro)-OH, or Fmoc-Thr(tBu)-Ser(Psi(Me,Me)pro)-OH is used.

The term "a position corresponding to a position selected from $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of SEQ ID NO: 1" as used herein refers to a position within the primary sequence of a glucagon-like peptide, which position is considered homologous to a position selected from $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of SEQ ID NO: 1, based on a sequence alignment of said glucagon-like peptide with the peptide of SEQ ID NO: 1.

Typically, the positions which are displayed on top of each other in such an alignment are considered to be homologous, i.e. to correspond to each other. Typical sequence alignment tools such as BLAST or ClustalW are well known to the person skilled in the art.

Optionally, the progress of the SPPS reaction may be monitored using in process controls to ensure efficient Fmoc removal, coupling, and/or capping steps. Fmoc determination on one hand and determination of free amines on the other hand may result in complementary information. Taken together, these methods may enable efficient monitoring of each step of the SPPS process. Some of the common monitoring methods usable in the context of the present invention are exemplified below.

Optionally, the amount of Fmoc cleaved from the resin-bound peptide may easily be quantified, e.g., by spectrometric determination. The Fmoc cleavage reagent drained from the resin may be collected and the Fmoc concentration therein determined, e.g. by measuring the absorbance at 301 nm. Based on the amount of Fmoc cleaved off, the resin load, i.e. the original amount of Fmoc peptide on the resin, may be calculated. Further, to assess the completeness of Fmoc removal, a small sample of presumably Fmoc-deprotected resin may be subjected to an additional harsh Fmoc cleavage protocol in order to determine the amount of residual Fmoc removed by this treatment. In the alternative, a small scale test cleavage of the peptide from a resin sample may be carried out in order to assess the completeness of Fmoc removal. The resulting peptides may be analyzed by analytical RP-HPLC using a standard gradient, where Fmoc protected and free peptide sequences are usually well separated. Additionally or alternatively, the peptide sample may be analyzed by mass spectrometry, e.g. by LC-MS or MALDI-MS. Thin layer chromatography likewise may enable the detection of minute amounts of Fmoc peptides.

The amount of free amines on the resin may be assessed by various assays, including the colorimetric Kaiser (i.e. Ninhydrin), TNBS, Chloranil, and Bromophenol Blue tests. This is well-known to a person skilled in the art.

These tests may advantageously be used to assess the generation of free amino functions after Fmoc-cleavage, as well as their disappearance after coupling of the following Fmoc-protected amino acid derivative and/or after a capping step. Preferably, at least two colorimetric tests such as the Kaiser and the TNBS tests may be carried out in parallel. The Kaiser test is based on the reaction of ninhydrin with amines. It is a very sensitive test for primary amines, visualized by an intense blue color, and somewhat less suitable for secondary amines, which yield a brownish red color. The color usually develops mainly in the beads and partly in the supernatant. When a spectrometric quantitation of the amount of unreacted amino groups is intended, the color may be transferred completely to the solution. The intensity of the color depends on the nature of the amino terminus to be detected. Rather unspecific shades are obtained with N-terminal, sidechain protected Asp, Asn, Cys, Ser, and Thr and brownish red beads result with N-terminal Pro. As the resin sample is typically heated, "hidden" $NH_2$-groups may become more accessible and thus detectable.

However, prolonged heating as well as overheating should be avoided as it may cause cleavage of Lys(Boc) or Fmoc removal (by pyridine). The TNBS (2,4,6-trinitrobenzenesulfonicacid) test is nearly as sensitive as the Kaiser test, but can only be used for detecting primary amino groups. Only the beads will turn orange-red and the intensity of the color does not depend on the nature of the N-terminal amino acid. As a slightly orange staining in the core of the beads cannot be detected by simple visual inspection, it is recommended to use more sensitive read-outs, e.g. to inspect the beads under a microscope.

Step d) of a method according to the present invention, i.e. the step of removing the Alloc protecting group from the resin-bound precursor peptide, so as to expose a free N-terminal alpha amino group, may be carried out by any means known in the art. Many such protocols have been described in the literature and often rely on the use of a catalyst such as $[Pd(PPh_3)_4]$=$Pd(Ph_3P)_4$, $Pd_2(dba)_3.CHCl_3$, $Pd(dba)_2$, $Pd(Ph_3P)_2Cl_2$, $(Ph_3P)_2NiCl_2$, or $Pd(OAc)_2$. For cleavage from a solid phase, the soluble $[Pd(PPh_3)_4]$ may be advantageous.

The amount of catalyst will be routinely optimized for any given reaction and may be, e.g., 0.002, 0.0025, 0.0030, 0.0035, 0.0040, . . . , 0.0100, . . . , 0.0200, . . . , 0.0300, . . . , 0.0400, . . . , 0.0500, . . . , 0.0600, . . . , 0.0700, . . . , 0.0800, . . . , 0.0900, . . . 0.1000, . . . , 0.1100, . . . , 0.1200, . . . , 0.1300, . . . , 0.1400, . . . , 0.1500, . . . , 01600, . . . 0.1700, . . . , 0.1800, . . . , 0.1900, . . . , 0.2000, . . . , 0.2100, . . . , 0.2200, . . . , 0.2300, . . . 0.2400, . . . , 0.2500, . . . , 0.2600, . . . , 0.2700, . . . , 0.2800, . . . , 0.2900, 0.3000, . . . 0.3100, . . . , 0.3200, . . . , 0.3300, . . . , 0.3400, . . . , 0.3500, . . . , 03600, . . . , 0.3700, . . . 0.3800, . . . , 0.3900, . . . , 0.4000, . . . 0.5000, . . . 0.6000, . . . 0.7000, . . . 0.8000, . . . 0.9000, . . . 1.0000, . . . 1.1000, . . . , or 1.2000 molar equivalents of the alloc group to be removed.

It may be combined with one or more allyl scavengers selected, e.g., from the group consisting of N,N-dimethyl-barbituric acid (NDMBA), Thiosalicylic acid, phenylsilane ($PhSiH_3$), $NaBH_4$, $Bu_4NBH_4$, $NH_3.BH_3$, dimethylamine borane-complex ($Me_2NH.BH_3$), t-$BuNH_2.BH_3$, $Me_3N.BH_3$, morpholine, or $Py.BH_3$. The amount of each scavenger will be routinely optimized for any given reaction and may be, e.g., 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0 equivalents of the alloc group to be removed.

It is preferable to swell the peptide resin in a solvent before adding the catalyst and scavengers. Said reagents may be added to the swollen resin in any order. Any suitable solvent, e.g. THF, DCM or DMF, may be used for swelling the resin and carrying out step d). For example, the swollen resin may be mixed with a solution comprising the scavenger(s) before adding the catalyst. Alternatively or additionally, a solution comprising the catalyst and scavengers may be added to the swollen resin. Step d) may be carried out under inert gas, e.g. under $N_2$ atmosphere.

In one embodiment of a method according to the present invention, 8.0-12.0 eq. dimethylamine borane-complex and/or 2.0-6.0 eq. morpholine are used as scavenger(s) with 0.002 eq.-1.1500 eq. [Pd(PPh$_3$)$_4$] as catalyst and DCM as solvent. In one embodiment of a method according to the present invention, 12.0-40.0 eq. dimethylamine borane-complex and/or 4.0-6.0 eq. morpholine are used as scavenger(s) with 0.02 eq.-1.15 eq. [Pd(PPh$_3$)$_4$] as catalyst and DMF as solvent. In one embodiment of a method according to the present invention, 15-20 eq. phenylsilane may be used as a scavenger with [Pd(PPh$_3$)$_4$] as catalyst and DCM as solvent. In one embodiment of a method according to the present invention, 15-20 eq. phenylsilane may be used as scavenger with [Pd(PPh$_3$)$_4$] as catalyst and DMF as solvent. In one embodiment of a method according to the present invention, 12.0-18.0 eq. dimethylamine borane-complex and/or 4.0-6.0 eq. morpholine are used as scavenger(s) with 0.02 eq.-1.15 eq. [Pd(PPh$_3$)$_4$] as catalyst and DCM as solvent. In one embodiment, 15-20 eq. phenylsilane may be used as a scavenger with [Pd(PPh$_3$)$_4$] as catalyst and DCM as solvent. In one embodiment of a method according to the present invention, 12.0-18.0 eq. dimethylamine borane-complex and/or 4.0-6.0 eq. morpholine are used as scavenger(s) with 0.02 eq.-1.15 eq. [Pd(PPh$_3$)$_4$] as catalyst and DCM as solvent under N$_2$ atmosphere. Alternatively, 15-20 eq. phenylsilane may be used as a scavenger with [Pd(PPh$_3$)$_4$] as catalyst and DCM as solvent under N$_2$ atmosphere.

In one embodiment of a method according to the present invention, step d) involves incubation of the solid-phase bound peptide obtained in step c) with a solution comprising [Pd(PPh$_3$)$_4$] and one or more scavengers.

In one embodiment of a method according to the present invention, said scavengers are selected from the group consisting of morpholine, dimethylamine borane-complex, and phenylsilane.

Preferably, step d) further involves extensive washing steps, wherein MeOH, DMF and IPA may be used. The washing steps may involve exposure of the resin-bound precursor peptide to small amounts of water or silica.

When the synthesis of the precursor peptide by SPPS is completed, it is still conjugated to the resin. Thus, it is solid phase bound and at least partly side-chain protected. To obtain the final peptide, e.g. semaglutide or any other glucacon-like peptide of the present invention, the peptide is cleaved off the resin. This is herein represented by step (f) of cleaving the peptide from the solid phase, typically, cleaving the semaglutide peptide from the solid phase and (concomitantly) cleaving the protecting groups from the semaglutide peptide (deprotection).

Most preferably, during this step, also most or all of the side chain protecting groups are concomitantly cleaved off the peptide, i.e., the peptide is deprotected, thereby providing the essentially unprotected peptide, preferably semaglutide.

Therefore, preferably, deprotection and cleavage from the resin (f) are carried out concomitantly by incubation with a cleavage composition comprising TFA and one or more scavengers.

For cleaving the peptide off the resin, any composition suitable for this purpose may be used. Preferably, cleavage and deprotection is conducted by means of a composition comprising more than 50% (v/v) TFA, more preferably more than 75% (v/v) TFA, in particular at least 80% (v/v) or even at least 90% (v/v) TFA.

The composition may also comprise water and/or one or more scavengers. Preferably, the composition comprises TFA, water and one or more scavengers. Particularly advantageous scavengers are thiol scavengers such as EDT and/or silane scavengers such as, e.g., TIPS.

The cleavage composition may comprise at least 80% TFA, preferably at least 90% TFA, and EDT. The cleavage composition may comprise at least 80% TFA, preferably at least 90% TFA, water, and EDT. The cleavage composition may comprise at least 80% TFA, preferably at least 90% TFA, water, and TIPS. The cleavage composition may comprise at least 80% TFA, preferably at least 90% TFA, water, TIPS and EDT. Exemplary, compositions for use in the context of the present invention may be selected from the group consisting of TFA/water/TIPS (90:5:5) v/v/v, TFA/water/phenol (90:5:5) v/v/v, TFA/water/EDT/TIPS (90:5:2.5:2.5) v/v/v/v, TFA/water/EDT/TIPS (90:4:3:3) v/v/v/v, TFA/water/EDT (90:5:5) v/v/v, TFA/thioanisole/anisole/EDT (90:5:3:2) v/v/v/v and TFA/thioanisole/water/phenol/EDT (82.5:5:5:5:2.5) v/v/v/v/v.

The step of cleaving the precursor peptide off the resin (step f) may be carried out at any conditions suitable for this purpose. Cleavage is preferably carried out (preferably under inert gas) by incubating the washed resin with the cleavage composition for about 1 to 4 h and/or at a temperature of 0 to 32° C. Exemplarily, cleavage may be carried out (preferably under inert gas) by incubating the washed resin with the cleavage composition for up to 1, up to 1.5, up to 2, up to 2.5, up to 3, up to 3.5 or up to 4 h or longer than 4 h at a temperature of about 0 to 4° C., 4 to 10° C., 10-15° C., 15 to 25° C., or 25 to 35° C. Exemplarily, cleavage may be carried out (preferably under inert gas) by incubating the washed resin with the cleavage composition for up to 1, up to 1.5, up to 2, up to 2.5, up to 3, up to 3.5 or up to 4 h or longer than 4 h at a temperature of about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32° C.

Alternatively, another cleavage composition may be used. For example, the cleavage of protected peptide fragments from 2-Chlorotrityl resin may be achieved using TFE/AcOH/DCM (1:1:3), 0.5% TFA/DCM, or HFIP/DCM.

The person skilled in the art will routinely optimize the compositions for use in the context of the present invention depending on the amino acid composition of the peptide in question and will envisage the optional use of one or more scavengers such as, inter alia, DTE, EDT, TES, TIPS, 2-mercaptoethanol, ethyl methyl sulfide, m- or p-cresol, 2-Me-indole, Ac-Trp-OMe, or tryptamine.

In the context of the present application, the term "scavengers" is used to refer to compounds which are added to the reaction mixture in order to suppress side reactions during cleavage of a peptide from the resin after SPPS and/or during removal of protecting groups. Typical scavengers used in a cleavage composition are "thiol scavengers" (e.g. EDT, DTE, DTT, and beta-mercaptoethanol) and "silane scavengers" (e.g. TES and TIPS). Further commonly used scavengers comprise ethyl methyl sulfide, thioanisole, anisole, m- or p-cresol, 2-Me-indole, Ac-Trp-OMe, or tryptamine. The person skilled in the art is well aware of a large variety of scavengers usable.

Incubation of the peptide resin with the cleavage composition results in a solution SO, which comprises the ingredients of the cleavage composition, the residuals of protecting groups cleaved off the peptide and the peptide. Preferably, the solution SO comprises TFA (typically at least 80% (v/v) or at least 90% (v/v)), water, one or more scavengers, the residuals of protecting groups cleaved off the peptide, and the peptide.

The resin is then separated, usually by filtration, from the solution SO obtained from step f), i.e., by cleaving the peptide from the solid phase, typically, cleaving the semaglutide peptide from the solid phase and (concomitantly) cleaving the protecting groups from the semaglutide peptide (deprotection). In an embodiment of the invention, said solution SO obtained from step f) comprises the semaglutide peptide and the regents used for cleavage (e.g., TFA, water, scavengers), and residuals of the protecting groups cleaved off the peptide. Optionally, the resin is rinsed after filtration, e.g. with concentrated TFA or with concentrated TFA plus scavengers. Optionally, the additional rinsing solutions may also form part of the solution SO obtained from step f), i.e., they may be pooled with the solution obtained directly after cleavage of the peptide from the resin.

The person skilled in the art will note that it is desirable to isolate the peptide of formula I from the solution SO, thereby obtaining a crude peptide (typically present as the TFA salt). In one embodiment of the present invention, this is performed by precipitation of the peptide from the solution SO by means of an anti-solvent and subsequently isolating the obtained precipitate.

As used herein, the term "anti-solvent" may be understood in the broadest sense as any reagent which induces peptide precipitation when mixed with a peptide solution. Exemplary, anti-solvents may comprise diethyl ether, IPE, MTBE, and mixtures of IPE with ACN. The anti-solvent may be mixed with solution SO by any means and in any order, i.e. the anti-solvent may be added to the solution SO or vice versa.

The precipitate comprising the semaglutide peptide is then formed as a suspension in the anti-solvent, wherein said suspension further comprises the reagents of the cleavage composition (e.g., TFA, water, and scavengers) as well as the residuals of the protecting groups cleaved off the peptide. The precipitate comprising (or essentially consisting of) the semaglutide peptide may then be isolated from the crude suspension by any means known for such purpose in the art.

According to a preferred embodiment, this step (iii) is accomplished by means of filtration and/or centrifugation.

As used herein the term "isolating" may be understood in the broadest sense as any means for obtaining a product of interest, e.g. a crude peptide precipitate, from a more complex composition. A crude peptide precipitate may comprise at least 30% (w/w), preferably at least 40% (w/w), more preferably at least 50% (w/w), more preferably at least 60% (w/w), more preferably at least 70% (w/w), even more preferably at least 80% (w/w), even more preferably at least 90% (w/w), in particular at least 95% (w/w) or even 100% (w/w) of the peptide of interest in the dry state. Typically, a crude peptide precipitate comprises 40-70% (w/w) of the peptide of interest, e.g. semaglutide, in the dry state.

Filtration may be any filtration method known in the art, such as, e.g., dead-end filtration or cross-flow filtration. As used herein, the terms "cross-flow filtration", "crossflow filtration", "tangential flow filtration" or "tangential filtration" may be understood interchangeably. The filter may be of any material known in the context of filtration in the art, such as, e.g., plastic (e.g., nylon, polystyrene), metal, alloy, glass, ceramics, cellophane, cellulose, or composite material. The filter may be hydrophobic or hydrophilic. The surface of the filter may be neutral or positively charged or negatively charged.

Centrifugation may be understood in the broadest sense as any means wherein the sedimentation of the suspended precipitate is accelerated. Exemplarily, a centrifugal force of up to 100×g, at least 100×g, at least 1,000×g, at least 2,500×g, at least 5,000×g, at least 7,500×g, at least 10,000× g, at least 15,000×g, at least 25,000×g, or at least at least 50,000×g may be used. By means of centrifugation, a cake comprising (or (essentially) consisting of) the crude semaglutide peptide is formed. Optionally, the cake may be resuspended in an anti-solvent which may be identical or different to the above-referenced anti-solvents. Optionally, centrifugation and resuspending the pellet in an anti-solvent may be reiterated several times which may increase the purity of the crude semaglutide peptide further.

Preferably, the crude peptide obtained by the method of the present invention can be subjected to further purification by one or more preparative process steps. Means for purification and separation, which may optionally be used in this context, comprise, e.g., one or more electrophoretic methods (e.g., gel electrophoresis or capillary (CE) electrophoresis), one or more additional precipitation-based methods (e.g., salting in or salting out), one or more dialytical methods (dialysis), and/or one or more chromatographic methods (e.g., gel permeation chromatography (GPC), size exclusion chromatography, Ion exchange chromatography (IEC), high performance liquid chromatography (HPLC), reversed phase HPLC (RP-HPLC), fast protein liquid chromatography (FPLC), Flash Chromatography (flash), Rapid Refluid Liquid Chromatography (RRLC), Rapid Separation Liquid Chromatography (RSLC), Ultra Fast Liquid Chromatography (UFLC), reversed phase UFLC (RP-UFLC), Ultra Performance Liquid Chromatography (UPLC) or reversed phase UPLC (RP-UPLC) Preferably, the crude peptide is first subjected to three-dimensional reversed phase HPLC followed by size exclusion chromatography, ion exchange chromatography, continuous chromatography, or ultrafiltration.

The peptide, e.g. the semaglutide peptide, synthesized according to an embodiment of the present invention may be purified by two dimensional RP-HPLC using a C8 or C18 hydrocarbon silica. For example, a mobile phase comprising acetonitrile and diluted $H_3PO_4$ may be used in the first dimension and a mobile phase comprising acetonitrile and diluted TFA may be used in the second dimension.

Another aspect of the present invention relates to a method for the full chemical synthesis of a semaglutide peptide, the method involving:
 a') Synthesizing a first solid-phase bound peptide of sequence SEQ ID NO: 1, wherein the Lys moiety in position 20 is amide bonded to an 8-amino-3,6-dioxaoctanoic acid moiety having an Alloc protected amino group, and the side chains of at least Glu and Asp carry protecting groups;
 b') Removing the Alloc group from said solid-phase bound peptide; and
 c') Acylating the resulting free amino group so as to obtain a solid-phase bound semaglutide peptide.

In the context of said precursor peptide, all definitions and explanations laid out above with respect to steps a), d), and b) are likewise applicable to steps a'), b') and c'), respectively. Preferably, step b') involves incubation of the solid-phase bound peptide obtained in step a') with a solution comprising [Pd(PPh$_3$)$_4$] and one or more scavengers, optionally selected from the group consisting of morpholine, dimethylamine borane-complex, and phenylsilane. Further, step a') is preferably carried out by SPPS using Fmoc-protected alpha amino acid derivatives, Fmoc-protected a dipeptide derivatives, and/or Fmoc protected pseudoproline dipeptide derivatives as building blocks. Further, step c') preferably involves performing SPPS using Fmoc-AEEAc-OH, Fmoc-Glu-OtBu, and octadecanedioic acid or octadecanedioic acid mono-t-butyl ester as building blocks.

A still further aspect of the present invention relates to a precursor peptide conjugated to a resin. In particular, the present invention provides a solid-phase bound peptide of the structure

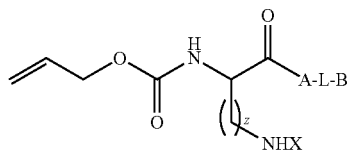

wherein:
B is a solid phase functionalized with any suitable linker structure L;
A is a peptide sequence of 0-100 amino acid moieties, optionally comprising side chain protecting groups;
z is selected from 1-10, preferably 4;
X is selected from an amino protecting group $R_1$, H, or a group selected from structures (iii) to (vi) below:

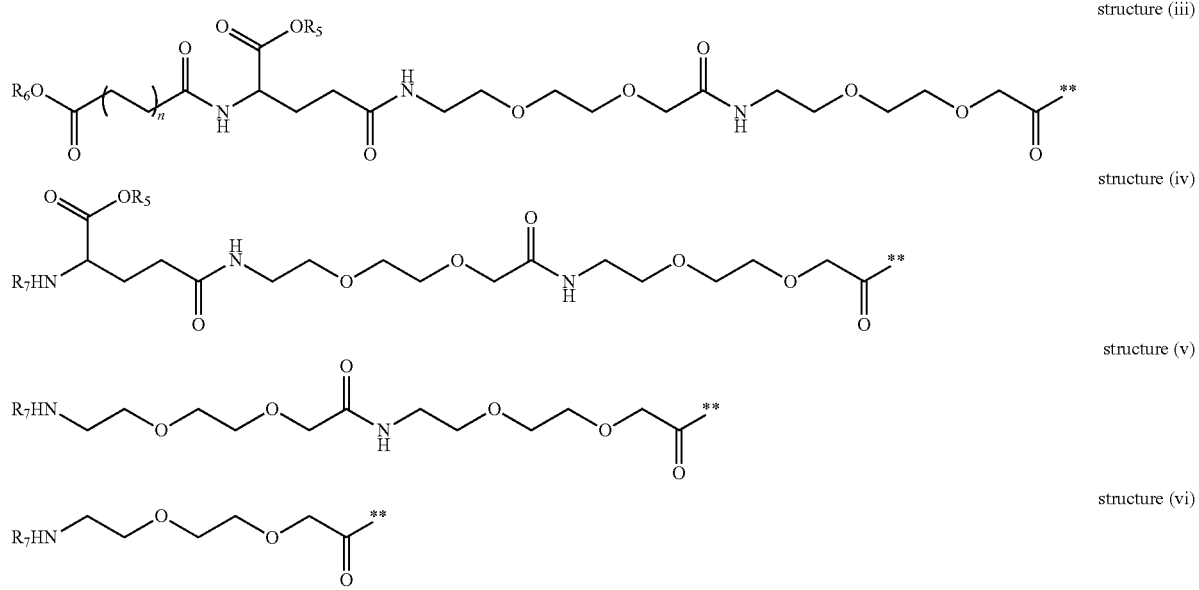

structure (iii)

structure (iv)

structure (v)

structure (vi)

wherein:
** denotes the point of attachment to the N atom of the amino side chain;
n is selected from 1-10, preferably 8;
$R_5$ and $R_6$ are the same or different and are H or a carboxyl protecting group moiety (i.e., a part of a carboxyl protecting group, thus, e.g., $R_5O$— or $R_6O$— each bound to —CO-peptide); and
$R_7$ is H or an amino protecting group, which may be the same as or different from $R_1$.
In preferred embodiments, $R_1$ and R7 are independently selected from the group consisting of H, 9-fluorenyl-methoxycarbonyl (Fmoc), t-butyloxycarbonyl (Boc), 4-methyltrityl (Mtt), 4-methoxytrityl (Mmt), or trityl (Trt). In further preferred embodiments, —$OR_5$ and —$OR_6$ are independently selected from the group consisting of —OH, —OtBu (t-butyl ester), and -OMPe (3-methylpent-3-yl ester).
In the context of said precursor peptide, all definitions and explanations laid out above also apply. The person skilled in the art will notice that also salts, in particular pharmaceutical acceptable salts, of said precursor peptides are also embraced by the present invention.

In a preferred embodiment, the solid phase bound precursor peptide is Alloc-Lys(Fmoc)-Glu(PG5)-Phe(PG4)-Ile-Ala-Trp(PG3)-Leu-Val-Arg(PG2)-Gly-Arg(PG1)-Gly-L-B, wherein B is a solid phase functionalized with any suitable linker structure L and PG1 through PG5 independently are absent or are side-chain protecting groups, which may be the same as or different from any of each other.

As used herein, the term "precursor peptide" may be understood in the broadest sense as a compound that can be converted into a peptide in the sense of the present invention, e.g., a glucagon-like peptide, in particular semaglutide. Typically, such a precursor is a product of SPPS, which is partly or fully protected at its side chains and conjugated to its resin, i.e., solid-phase conjugated.

The present invention also relates to a peptide, in particular a semaglutide peptide, as obtainable from the methods of the present invention.

In the methods of the present invention, removal of the alloc group from the alpha amino function may lead to the formation of specific side products of the general formula (viii):

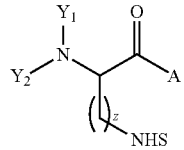

Formula (viii)

wherein:
z is an integer from 0 to 10;
A is any peptide sequence of 1 to 100 amino acids, which optionally carry side chain protecting groups;

S is any substituent to the amino group;

Y$_1$ is an allyl group; and

Y$_2$ is an allyl group or is a N-terminal amino acid sequence of 1 to 100 amino acids, which optionally carry side chain protecting groups.

For example, the side product may be of the formula His-Aib-Glu-Gly-Thr-Phe-Thr-Ser-Asp-Val-Ser-Ser-Tyr-Leu-Glu-Gly-Gln-Ala-Ala-(N$^\alpha$-allyl)-Lys(AEEAc-AEEAc-γ-Glu-17-carboxyheptadecanoyl)-Glu-Phe-Ile-Ala-Trp-Leu-Val-Arg-Gly-Arg-Gly-OH and/or of the formula (N$^\alpha$-allyl)$_2$-Lys(AEEAc-AEEAc-γ-Glu-17-carboxyheptadecanoyl)-Glu-Phe-Ile-Ala-Trp-Leu-Val-Arg-Gly-Arg-Gly-OH.

A peptide obtainable by a method according to the present invention is therefore characterized in that it contains detectable levels of an impurity of the formula (viii):

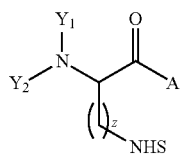

Formula (viii)

wherein:

z is an integer from 0 to 10;

A is any peptide sequence of 1 to 100 amino acids, which optionally carry side chain protecting groups;

S is any substituent to the amino group;

Y1 is an allyl group; and

Y2 is an allyl a N-terminal amino acid sequence of 1 to 100 amino acids, which optionally carry side chain protecting groups In one embodiment, the present invention relates to a semaglutide peptide characterized in that it contains detectable levels of an impurity of the formula His-Aib-Glu-Gly-Thr-Phe-Thr-Ser-Asp-Val-Ser-Ser-Tyr-Leu-Glu-Gly-Gln-Ala-Ala-(N$^\alpha$-allyl)-Lys(AEEAc-AEEAc-γ-Glu-17-carboxyheptadecanoyl)-Glu-Phe-Ile-Ala-Trp-Leu-Val-Arg-Gly-Arg-Gly-OH and/or of the formula (N$^\alpha$-allyl)$_2$-Lys(AEEAc-AEEAc-γ-Glu-17-carboxyheptadecanoyl)-Glu-Phe-Ile-Ala-Trp-Leu-Val-Arg-Gly-Arg-Gly-OH.

For example, a peptide according to the present invention preferably comprises traces (e.g., 0.001 ppm (w/w) or more, 0.01 ppm (w/w) or more, or 0.1 ppm (w/w) or more, or 1 ppm (w/w) or more) of such impurities.

The person skilled in the art will use routine experimentation to detect and optionally quantify the impurity in question. This will commonly involve, but is not limited to, the use of mass spectrometry and/or analytical chromatography, e.g. reversed phase chromatography, ion exchange chromatography, size exclusion chromatography, normal phase chromatography, or ion pair chromatography, according to the established guidelines set out, e.g., in the US pharmacopeia and/or as corresponds to the state of the art in the field of analytical chemistry. For example, RP-HPLC in combination with UV detection or mass spectrometry may be used. Independent on the detection means (e.g. UV detector or mass spectrometer), the quantity of the impurity may be expressed in relative terms (e.g. 0.01 area %) or in absolute terms (e.g. 0.01% w/w).

The methods of the present invention are suitable to reduce these impurities to a minimum.

Therefore, in one embodiment, the present invention relates to a semaglutide peptide characterized in that it contains detectable levels, but below 0.50% of an impurity of the formula His-Aib-Glu-Gly-Thr-Phe-Thr-Ser-Asp-Val-Ser-Ser-Tyr-Leu-Glu-Gly-Gln-Ala-Ala-(N$^\alpha$-allyl)-Lys(AEEAc-AEEAc-γ-Glu-17-carboxyheptadecanoyl)-Glu-Phe-Ile-Ala-Trp-Leu-Val-Arg-Gly-Arg-Gly-OH and/or of the formula (N$^\alpha$-allyl)$_2$-Lys(AEEAc-AEEAc-γ-Glu-17-carboxyheptadecanoyl)-Glu-Phe-Ile-Ala-Trp-Leu-Val-Arg-Gly-Arg-Gly-OH. In one embodiment, the present invention relates to a semaglutide peptide characterized in that it contains between 0.01% and 0.50% of an impurity of the formula His-Aib-Glu-Gly-Thr-Phe-Thr-Ser-Asp-Val-Ser-Ser-Tyr-Leu-Glu-Gly-Gln-Ala-Ala-(Nα-allyl)-Lys(AEEAc-AEEAc-γ-Glu-17-carboxyheptadecanoyl)-Glu-Phe-Ile-Ala-Trp-Leu-Val-Arg-Gly-Arg-Gly-OH and/or of the formula (N$^\alpha$-allyl)$_2$-Lys(AEEAc-AEEAc-γ-Glu-17-carboxyheptadecanoyl)-Glu-Phe-Ile-Ala-Trp-Leu-Val-Arg-Gly-Arg-Gly-OH.

In other embodiments, the peptide obtainable according to the methods of the present invention contains between 0.01% and 5%, 0.01% and 0.50%, 0.01% and 0.40%, 0.01% and 0.30%, 0.01% and 0.02%, or 0.01 and 0.01% of at least one impurity as defined above. In certain embodiments, the peptide obtainable according to the methods of the present invention contains between 0.005% and 5%, 0.005% and 0.5%, 0.005% and 0.4%, 0.005% and 0.3%, 0.005% and 0.2%, or 0.005 and 0.1% of at least one impurity as defined above.

Preferably, the percentage of any impurity is determined as the relative content observed by mass spectrometry or by analytical reversed phase HPLC (RP-HPLC), e.g. with UV detection at e.g. 220 nm and/or with detection by mass spectrometry.

The relative content is usually determined as relative peak area or relative signal intensity, i.e. area or intensity % of a given peak area or signal intensity divided by the sum of the areas or intensities of all observed peaks or signals in a chromatogram or mass spectrum. In another preferred embodiment, the percentage of any impurity is determined as the absolute content observed by mass spectrometry or by analytical reversed phase HPLC (RP-HPLC), e.g. with UV detection at e.g. 220 nm and/or with detection by mass spectroscopy. The absolute content is usually indicated as % (w/w) relative to the total mass of a sample, and may be preferably determined by comparison with an external standard. In one embodiment, the percentage of the impurity is determined as the relative peak area observed in analytical RP-HPLC with UV detection at 220 nm. Any product-specific RP-HPLC protocol suitable for the detection of peptidic contaminants may be used. The suitability of the analytic method is routinely assessed in terms of principal peak purity determined by LC-MS. The person skilled in the art will immediately understand that, due to their similar structure, all peptidic components have the same or at least comparable response factors, such that the relative peak area measured by RP HPLC at e.g. 220 nm correlates well to the relative abundance of a given peptide expressed in weight percent relative to the summed mass of all peptide components, indicated in % (m/m). Alternatively, the percentage of any impurity may be determined by mass spectrometry.

Therefore, in preferred embodiments, the peptide obtainable according to the methods of the present invention contains between 0.01% and 5%, 0.01% and 0.50%, 0.01% and 0.40%, 0.01% and 0.30%, 0.01% and 0.02%, or 0.01 and 0.01% of at least one of the above-defined impurities, determined as the relative peak area observed in analytical RP-HPLC with UV detection at 220 nm and/or mass spectroscopy. In other preferred embodiments, the peptide obtainable according to the methods of the present invention contains between 0.01% (w/w) and 5% (w/w), 0.01% (w/w) and 0.50% (w/w), 0.01% (w/w) and 0.40% (w/w), 0.01% (w/w) and 0.30% (w/w), 0.01% (w/w) and 0.2% (w/w), or 0.01% (w/w) and 0.1% (w/w) of at least one of the above-defined impurities.

Moreover, the present invention provides a pharmaceutical composition comprising a peptide, e.g. a glucagon-like peptide, produced according to the methods of the present invention.

Therefore, a further aspect of the present invention refers to a pharmaceutical composition comprising:

(A) a semaglutide peptide obtainable from a method according to the present invention, and (B) a pharmaceutically acceptable carrier.

A pharmaceutically acceptable carrier may be any additive or composition of additives known for this purpose. Such additive may exemplarily be a non-toxic solvent such as, e.g., water, dimethyl sulfoxide (DMSO), ethanol, vegetable oil, paraffin oil or combinations thereof. Furthermore, a carrier may contain one or more detergents, one or more foaming agents (e.g., sodium lauryl sulfate (SLS)/sodium doceyl sulfate (SDS)), one or more coloring agents (e.g., $TiO_2$, food coloring), one or more vitamins, one or more salts (e.g., sodium, potassium, calcium, zinc salts), one or more humectants (e.g., sorbitol, glycerol, mannitol, propylenglycol, polydextrose), one or more enzymes, one or more preserving agents (e.g., benzoic acid, methylparabene), one or more texturing agents (e.g., carboxymethyl cellulose (CMC), polyethylene glycol (PEG), sorbitol), one or more emulsifiers, one or more bulking agents, one or more glacing agents, one or more separating agents, one or more antioxidants, one or more herbal and plant extracts, one or more stabilizing agents, one or more polymers (e.g., hydroxypropyl methacrylamide (HPMA), polyethylene imine (PEI), carboxymethyl cellulose (CMC), polyethylene glycol (PEG)), one or more uptake mediators (e.g., polyethylene imine (PEI), dimethyl sulfoxide (DMSO), a cell-penetrating peptide (CPP), a protein transduction domain (PTD), an antimicrobial peptide, etc.) one or more antibodies, one or more sweeteners (e.g., sucrose, saccharin Na, *stevia*), one or more counterstain dyes (e.g., fluorescein, fluorescein derivatives, Cy dyes, an Alexa Fluor dyes, S dyes, rhodamine, quantum dots, etc.), one or more homeopathic ingredients one or more gustatory substances and/or one or more fragrances.

Yet another aspect of the present disclosure relates to a method for the full chemical synthesis of a semaglutide peptide, the method involving:

a') Synthesizing a first solid-phase bound peptide of sequence SEQ ID NO:1, wherein the Lys moiety in position 20 is amide bonded to an 8-amino-3,6-dioxa-octanoic acid moiety having an Alloc protected amino group, and the side chains of at least Glu and Asp carry protecting groups;

b') Removing the Alloc group from said solid-phase bound peptide; and c') Acylating the resulting free amino group so as to obtain a solid-phase bound semaglutide peptide.

Step a') may be carried out by SPPS using Fmoc-protected alpha amino acid derivatives, Fmoc-protected a dipeptide derivatives, and/or Fmoc protected pseudoproline dipeptide derivatives as building blocks. Step b') may involve incubation of the solid-phase bound peptide obtained in step a') with a solution comprising [Pd(PPh3)4] and one or more scavengers. Step c') may be performed by stepwise solid-phase synthesis using Fmoc-AEEAc-OH, Fmoc-Glu-OtBu, and octadecanedioic acid or octadecanedioic acid mono-t-butyl ester as building blocks.

The following Examples, including the experiments conducted and the results achieved, and the claims further illustrate the invention.

Sequence Listing semaglutide, a glucagon-like peptide 1 (GLP1) analogue:
H(Aib)EGTFTSDVSSYLEGQAAKEFIAWLVRGRG (SEQ ID NO: 1)

glucagon-like peptide 1 (GLP1) wild type peptide:
HAEGTFTSDVSSYLEGQAAKEFIAWLVKGRG (SEQ ID NO: 2)

EXAMPLES

General Methods

Analytical HPLC

Samples were analyzed on a C18 stationary phase using a mobile phase comprising 0.05% TFA (v/v) and acetonitrile. The acetonitrile gradient was from about 30% to about 60% (v/v) within 30 min. This gradient was designed to resolve impurities with elution characteristics similar to the product, which may become challenging during work-up of the crude peptide.

Solid Phase Peptide Synthesis (SPPS) of the Peptide Backbone

The synthesis was performed on preloaded H-Gly-2-chlorotrityl resin using a fully automated peptide synthesizer. Coupling reactions were carried out applying standard Fmoc-amino acid derivatives and Fmoc-dipeptide derivatives with DIC/Oxyma or TBTU/DIPEA as coupling reagents/additives in DMF as solvent. Fmoc-deprotection was carried out using a solution of 20% piperidine in DMF. DMF and IPA were used as solvents for washing steps. After each coupling, an acetylation step was performed routinely. The peptide was cleaved from the resin by incubation with TFA/H2O/TIPS (90:5:5, v/v/v) or TFA/EDT/water (90:5:5, v/v/v) separated from the resin by filtration, and precipitated on cold IPE.

Removal of Alloc Protecting Group

The Alloc-deprotection was performed for 30 to 360 min at room temperature in a manual SPPS reactor using 12.0-18.0 eq. dimethylamine borane-complex and/or 4.0-6.0 eq. morpholine as scavenger(s) with 0.02 eq.-1.15 eq. [Pd(PPh$_3$)$_4$] as catalyst and DCM as solvent under N$_2$ atmosphere. Washing steps included MeOH, DMF and IPA. Alternatively, 15-20 eq. phenylsilane may be used as a scavenger with [Pd(PPh$_3$)$_4$] as catalyst and DCM as solvent under N$_2$ atmosphere.

Acylation of Side Chain Amino Groups

Amino acid or peptide side chain amino groups were acylated using one of the two protocols below.

Protocol a):

After deprotection of the side chain amino group of the peptide resin, stepwise manual or automated SPPS was carried out using Fmoc-AEEAc-OH, Fmoc-Glu-OtBu, and either octadecanedioic acid or octadecanedioic acid mono-t-butyl ester. DIC/Oxyma or TBTU/DIPEA coupling chemistry was employed and the coupling time was 18-22 h or 2-16 h.

After each coupling, an acetylation step was performed routinely. Fmoc was cleaved by incubation with 20% piperidine in DMF, followed by extensive washes with DMF and/or IPA.

Protocol b):

The protected side chain sequence fragment was synthesized by manual SPPS on a pre-loaded H-AEEAc-2-chlorotrityl resin, using essentially the same conditions as set out for protocol a). The fragment, e.g. mono-tBu-carboxyheptadecanoyl-γ-Glu(OtBu)-AEEAc-AEEAc-OH, was then cleaved using HFIP in DCM and concentrated before coupling using EDC, HOSu, and DIPEA in DMF. Alternatively, DIC/Oxyma or TBTU/DIPEA may be used as coupling reagents.

Preparative HPLC

The crude peptide was purified by two dimensional RP-HPLC using a C8 hydrocarbon bonded silica (10 micrometer particle diameter, pore size 100 Å). 0.1% $H_3PO_4$ aq. as eluent system containing ACN as organic modifier was used as a mobile phase in the first dimension, 0.1% TFA aq. containing ACN as organic modifier was used in the second dimension.

Example 1: Full Chemical Synthesis of Semaglutide

SPPS of the semaglutide backbone sequence was performed on preloaded H-Gly-2-chlorotrityl resin using a fully automated peptide synthesizer. Coupling reactions were carried out applying Fmoc-AA derivatives (including Fmoc-Lys(Alloc)-OH) or Fmoc-dipeptide derivatives and DIC/Oxyma or TBTU/DIPEA as coupling reagents/additives in DMF as solvent. Fmoc-deprotection was carried out using a solution of 20% piperidine in DMF. DMF and IPA were used as solvents for washing steps. After each coupling, an acetylation step was performed. The SPPS was carried out on 30 mmol scale. Crude material obtained from a test cleavage showed 45.4% U-HPLC purity.

Alloc-deprotection was performed as outlined in the general methods above for 30 min at room temperature in a manual SPPS reactor using morpholine and dimethylamine borane-complex as scavengers with [Pd(PPh$_3$)$_4$] as catalyst and DCM as solvent under $N_2$ atmosphere.

The side chain amino group was acylated according to protocol a) above. Semaglutide was cleaved from the peptidyl resin by incubation with TFA/EDT/water (90:5:5), separated from the resin by filtration, and precipitated on cold IPE. The resulting crude material showed 36.1% HPLC purity determined with the above analytical protocol (or 45.5% U-HPLC purity). Liquid chromatography mass spectrometry revealed two species (relative peak area: 3.1% and 1.0%) with M+40, which are considered to correspond to (N$^\epsilon$-allyl)-Lys derivatives of semaglutide.

Example 2: Full Chemical Synthesis of Semaglutide

The synthesis was performed on a preloaded H-Gly-2-chlorotrityl resin using a fully automated or manual peptide synthesizer and Fmoc-Lys(AEEAc-AEEAc-(γ-Glu-OtBu)-17-t-butoxycarboxyheptadecanoyl)-OH as a building block. This latter moiety may be synthesized according to protocol b) above. Coupling reactions were carried out applying Fmoc-amino acid derivatives or Fmoc-dipeptide derivatives and DIC/Oxyma or TBTU/DIPEA as coupling reagents/additives in DMF as solvent.

Fmoc-deprotection was carried out using a solution of 20% piperidine in DMF (v/v). DMF and IPA were used as solvents for washing steps. After each coupling, an acetylation step was performed. The SPPS was carried out on 1.66 mmol scale. Semaglutide was cleaved from the peptidyl resin by incubation with TFA/EDT/water (90:5:5, v/v/v), separated from the resin by filtration, and precipitated on cold IPE. The resulting crude material showed ~39.1% HPLC purity determined the above analytical protocol.

Example 3: Full Chemical Synthesis of Semaglutide

The peptidyl moiety corresponding to amino acids 31-20 of the semaglutide backbone was synthesized on a preloaded H-Gly-2-chlorotrityl resin using standard Fmoc-amino acid derivatives and Alloc-Lys(Fmoc)-OH as starting materials. Coupling reactions were carried out applying Fmoc-amino acid derivatives and DIC/Oxyma or TBTU/DIPEA as coupling reagents/additives in DMF as solvent. Fmoc-deprotection was carried out using a solution of 20% piperidine in DMF (v/v).

DMF and IPA were used as solvents for washing steps. After each coupling, an acetylation step was performed. Acylation of the epsilon amino group was performed by stepwise Fmoc-SPPS, essentially according to protocol a) above.

After completion of the side-chain synthesis, the Alloc group was removed from the alpha amino group of the Lys moiety as set out in the general methods above.

Subsequently, the sequence corresponding to amino acids 1-19 of the semaglutide sequence was added by SPPS. Coupling reactions were carried out applying Fmoc-AA derivatives or Fmoc-dipeptide derivatives and DIC/Oxyma as coupling reagents/additives in DMF as solvent. Fmoc-deprotection was carried out using a solution of 20% piperidine in DMF. DMF and IPA were used as solvents for washing steps. After each coupling, an acetylation step was performed. The peptide was cleaved from the resin as set out in the general methods above. The resulting crude material showed 42.1% HPLC purity determined with the above analytical protocol. Liquid chromatography mass spectrometry revealed one species (relative peak area 1.6%) with M+40, which is considered to correspond to a (N-allyl)-Lys derivative of semaglutide. More precisely, it is expected to be a (Nα-allyl)-Lys derivative of semaglutide.

Upon two dimensional purification of the crude peptide by RP-HPLC, the impurity was reduced to trace amounts.

Example 4: Full Chemical Synthesis of Semaglutide

The synthesis of the complete semaglutide backbone will be performed on preloaded H-Gly-2-chlorotrityl resin using a fully automated peptide synthesizer and Fmoc-Lys(AEEAc-Alloc)-OH as a building block. This latter moiety may be synthesized according to protocol b) above. Coupling reactions will be carried out applying Fmoc-amino acid derivatives or Fmoc-dipeptide derivatives and DIC/Oxyma or TBTU/DIPEA as coupling reagents/additives in DMF as solvent. Fmoc-deprotection will be carried out using a solution of 20% piperidine in DMF (v/v). DMF and IPA will be used as solvents for washing steps. After each coupling, an acetylation step will be performed.

After removal of the Alloc group according to the general protocol above, the resulting free amino group will be reacted with Fmoc-AEEAc-OH, Fmoc-Glu-OtBu, and subsequently (second) with either octadecanedioic acid or octadecanedioic acid mono-t-butyl ester as set out in general protocol a) above. Semaglutide will be cleaved from the peptidyl resin, separated from the resin by filtration, and precipitated on cold IPE.

Example 5: Full Chemical Synthesis of Semaglutide

The peptidyl moiety corresponding to amino acids 31-20 of the semaglutide backbone will be synthesized on a preloaded H-Gly-2-chlorotrityl resin using standard Fmoc-amino acid derivatives and Alloc-Lys(AEEAc-Fmoc)-OH as starting materials.

Coupling reactions will be carried out applying Fmoc-amino acid derivatives and DIC/Oxyma or TBTU/DIPEA as coupling reagents/additives in DMF as solvent. Fmoc-deprotection will be carried out using a solution of 20% piperidine in DMF (v/v). DMF and IPA will be used as solvents for washing steps. After each coupling, an acetylation step will be performed.

Next, acylation of the epsilon amino group will be performed by stepwise Fmoc-SPPS, according to protocol a) above.

After completion of the side-chain synthesis, the Alloc group will be removed from the alpha amino group of the Lys moiety as set out in the general methods above. Subsequently, the sequence corresponding to amino acids 1-19 of the semaglutide sequence will be added by SPPS and the peptide will be cleaved from the resin as set out in the general methods above.

---

---

The invention claimed is:

1. A method for the full chemical synthesis of a semaglutide peptide, the method involving:
   a) providing a first solid-phase bound peptide sequence of the formula (i)

Formula (i)

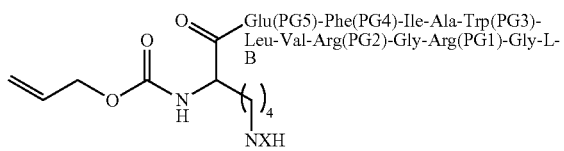

wherein:
X is an amino protecting group $R_1$ or is an amide bonded 8-amino-3,6-dioxa-octanoic acid moiety having an $R_1$ protected amino group (AEEAc-$R_1$);
B is a solid phase functionalized with any suitable linker structure L; and
PG1 through PG5 independently are absent or are side-chain protecting groups, which may be the same as or different from any of each other;

b) removing the protecting group $R_1$ so as to expose a free amino group;

c) acylating said free amino group so as to obtain a second solid-phase bound peptide sequence of the formula (ii), wherein $R_5$ and $R_6$ are the same or different and are H or a carboxyl protecting group moiety;

Formula (ii)

[Chemical structure of Formula (ii) showing: Allyl-O-C(=O)-HN- attached to a peptide chain labeled Glu(PG5)-Phe(PG4)-Ile-Ala-Trp(PG3)-Leu-Val-Arg(PG2)-Gly-Arg(PG1)-Gly-L-B, with linker containing HN groups, ether linkages, and a long fatty acid chain with $R_5O$ and $R_6O$ carboxyl groups]

d) removing the Alloc protecting group from the N-terminus of the solid phase bound peptide of formula (ii), so as to expose a free N-terminal alpha amino group;

e) coupling, by stepwise solid-phase peptide synthesis, the amino acid sequence $R_7$-His(PG19)-Aib-Glu(PG18)-Gly-Thr(PG17)-Phe(PG16)-Thr(PG15)-Ser(PG14)-Asp(PG13)-Val-Ser(PG12)-Ser(PG11)-Tyr(PG10)-Leu-Glu(PG9)-Gly-Gln(PG8)-Ala-Ala- to said free N-terminal alpha amino group so as to obtain a solid-phase bound semaglutide peptide, wherein:
PG8 to PG19 independently are absent or are side-chain protecting groups, which may be the same as or different from any of each other, any of PG1 to PG7, or both; and
$R_7$ is H or an amino protecting group, which may be the same as or different from $R_1$; and f) cleaving the semaglutide peptide from the solid phase.

2. The method according to claim 1, wherein step d) involves incubation of the solid-support bound peptide obtained in step c) with a solution comprising [Pd(PPh$_3$)$_4$] and one or more scavengers.

3. The method according to claim 2, wherein the scavengers are selected from the group consisting of morpholine, dimethylamine borane-complex, and phenylsilane.

4. The method according to claim 1, further wherein at least one of step a), step c), or steps a) and c) involve(s) stepwise solid phase peptide synthesis.

5. The method according to claim 1, wherein each of steps a), c) and e) involves solid phase peptide synthesis.

6. The method according to claim 1, wherein solid phase peptide synthesis is performed using building blocks, which comprise a free carboxyl group or an activated ester of a carboxyl group, an $R_1$ protected amino group, and optionally further protecting groups, and wherein the steps of:
i) coupling a building block, which comprises an $R_1$ protected amino group, to a free amino group generated in a previous step; and
ii) removal of $R_1$ to expose a free amino group are carried out in repeated cycles.

7. The method according to claim 1, wherein $R_1$ is a 9-fluorenyl-methoxycarbonyl (Fmoc) group.

8. The method according to claim 7, wherein step b) is performed by incubating the compound of formula (i) with a mixture selected from the group consisting of 5-50% (v/v) piperidine or 4-methyl piperidine in N,N-dimethylformamide (DMF), 5-50% (v/v) piperidine or 4-methyl piperidine in N-methylpyrrolidone (NMP), 1-5% (v/v) 3,5 diazabicyclo[5.4.0]undec-7-ene (DBU) in DMF, and 50% (v/v) morpholine in DMF.

9. The method according to claim 7, wherein step c) is performed by stepwise solid-phase synthesis using Fmoc-AEEAc-OH, Fmoc-Glu-OtBu, and octadecanedioic acid or octadecanedioic acid mono-t-butyl ester as building blocks.

10. The method according to claim 7, wherein each building block used in step a), step e) or steps a) and e) is selected independently from the group consisting of:
1) derivatives of alpha-amino acids, wherein the alpha amino group is protected by Fmoc, optionally further wherein the amino acid side chain carries a protecting group;
2) Alloc-Lys(Fmoc)-OH;
3) dipeptide derivatives, which comprise an Fmoc or Boc protected amino group, optionally further wherein at least one amino acid side chain carries a protecting group; and
4) a combination of two or all of 1) to 3).

11. The method according to claim 1, wherein one or more $R_1$-protected pseudoproline dipeptide derivative(s) is/are used in step e).

12. The method according to claim 11, wherein the $R_1$-protected pseudoproline dipeptide derivative(s) is/are selected from Fmoc-Gly-Thr(Psi(Me,Me)pro)-OH, Fmoc-Thr(tBu)-Ser(Psi(Me,Me)pro)-OH, Fmoc-Val-Ser(Psi(Me,Me)pro)-OH, Fmoc-Ser(tBu)-Ser(Psi(Me,Me)pro)-OH, and Fmoc-Phe-Thr(Psi(Me,Me)pro)-OH.

13. The method according to claim 1, wherein all of steps a), d), and e) are carried out by means of Fmoc solid-phase synthesis.

14. The method according to claim 1, wherein at least one of steps a), c), and e) comprises activating the building blocks used by means of one or more coupling reagent mixtures comprising reagents selected for each coupling reaction independently from the group consisting of:
(A) (benzotriazolyl)tetramethyluronium tetrafluoroborate (TBTU) plus diisopropylethylamine (DIPEA);
(B) diisopropylcarbodiimide (DIC) plus cyano-hydroxy-imino-acetic acid ethyl ester (Oxyma);
(C) 3-(diethoxy-phosphoryloxy)-3H-benzo[d][1,2,3]triazin-4-one (DEPBT) plus DIPEA;
(D) DIC plus hydroxybenzotriazole (HOBt);
(E) N-[(7-Aza-1H-benzotriazol-1-yl) (dimethylamino)-methylene]-N-methylmethanaminium tetrafluoroborate N-oxide (TATU) plus DIPEA;
(F) 2-(1H-benzotriazol-1-yl)-1,1,3,3-tetramethyluronium hexafluorophosphate (HBTU) plus DIPEA; and
(G) N-[(7-Aza-1H-benzotriazol-1-yl) (dimethylamino)-methylene]-N-methylmethanaminium hexafluorophosphate N-oxide (HATU) plus DIPEA.

15. The method according to claim 1, further wherein protecting groups are cleaved from the semaglutide peptide.

16. The method according to claim 1, wherein all side chain protecting groups, protecting groups bound to the alpha carboxyl group or both of the building blocks used are orthogonal to $R_1$ and Alloc.

17. The method according to claim 1, wherein the side chain protecting groups, protecting groups bound to the alpha carboxyl group or both of the building blocks used are independently selected from the group consisting of 2,2,5,7,8-pentamethylchroman-6-sulfonyl (Pmc), 2,2,4,6,7-pentamethyldihydrobenzofuran-5-sulfonyl (Pbf), 2,3,6-trimethyl-4-methoxybenzenesulfonyl (Mtr), t-butyl (tBu), trityl (Trt), 4-methoxytrityl (Mmt), 4-methyltrityl (Mtt), t-butyl ester (OtBu), 3-methylpent-3-yl ester (OMpe), 2-phenyl isopropyl (OPp), t-butoxycarbonyl (Boc), 2-(4,4-dimethyl-2,6-dioxocyclohexylidene)ethyl (Dde), and 1-(4,4-dimethyl-2,6-dioxocyclohex-1-ylidene) isovaleryl (ivDe).

* * * * *